United States Patent
Omura et al.

(10) Patent No.: US 8,080,581 B2
(45) Date of Patent: Dec. 20, 2011

(54) COSMETICS

(75) Inventors: Takayuki Omura, Yokohama (JP); Susumu Yoshida, Yokohama (JP); Yuko Nakanishi, Yokohama (JP); Hiroyuki Kakoki, Yokohama (JP)

(73) Assignee: Shiseido Company Ltd., Chuo-ku, Toyko (JP)

( * ) Notice: Subject to any disclaimer, the term of this patent is extended or adjusted under 35 U.S.C. 154(b) by 389 days.

(21) Appl. No.: 12/519,442

(22) PCT Filed: Dec. 26, 2007

(86) PCT No.: PCT/JP2007/075007
§ 371 (c)(1),
(2), (4) Date: Jun. 16, 2009

(87) PCT Pub. No.: WO2008/078787
PCT Pub. Date: Jul. 3, 2008

(65) Prior Publication Data
US 2010/0010241 A1 Jan. 14, 2010

(30) Foreign Application Priority Data
Dec. 26, 2006 (JP) .................. 2006-350365

(51) Int. Cl.
*A61K 31/355* (2006.01)
*C07D 311/72* (2006.01)

(52) U.S. Cl. ....... 514/458; 514/844; 549/408; 424/70.1; 424/70.31

(58) Field of Classification Search ............ 514/458, 514/844; 549/408
See application file for complete search history.

(56) References Cited

U.S. PATENT DOCUMENTS
| | | | |
|---|---|---|---|
| 5,235,073 A | 8/1993 | Kim et al. | |
| 5,869,703 A | 2/1999 | Kim et al. | |
| 6,045,826 A | 4/2000 | Borowy-Borowski et al. | |
| 6,355,811 B1 | 3/2002 | Kim et al. | |

OTHER PUBLICATIONS

Patent Abstract for Japanese Publication No. 55-013214 published Jan. 30, 1980, one page.
Patent Abstract for Japanese Publication No. 2003-277392 published Oct. 2, 2003, 14 pages.
International Search Report for corresponding PCT/JP2007/075007 mailed Feb. 5, 2008, two pages.
International Preliminary Report on Patentability for corresponding PCT/JP2007/075007 mailed Jul. 9, 2009, seven pages.

*Primary Examiner* — Bernard Dentz
(74) *Attorney, Agent, or Firm* — Rankin, Hill & Clark LLP

(57) ABSTRACT

The present invention provides a cosmetic having equal to or a higher antioxidant activity and moisture retaining property than the above-described conventional vitamin E derivatives. The cosmetic also has an excellent emulsifying ability and solubilizing ability and remarkably reduces a sticky feeling on the skin (in particular, the sticky feeling during drying after the application on the skin). That is, the cosmetic of the present invention containing a vitamin E derivative represented by the following formula (I) or a salt thereof.

$$R_4O-(EO)_k-(BO)_m-(EO)_n-\text{[chroman ring with }R_1, R_2, R_3\text{ substituents and phytyl side chain]}$$

[In the formula, $R_1$, $R_2$, and $R_3$ represent a hydrogen atom or a methyl group; $R^4$ represents a $C_{1-6}$ alkanoyl group, a $C_{1-6}$ alkyl group, a $SO_3H$ group, a $P(O)(OH)_2$ group, a $CH_2COOH$ group or a $COCH_2CH(SO_3H)COOH$ group; EO represents an ethylene oxide group; BO represents a butylene oxide group; k and n independently represent any one of numbers 0 to 30; and m represents any one of numbers 1 to 30.]

16 Claims, 1 Drawing Sheet

COSMETICS

RELATED APPLICATIONS

This application claims the priority of Japanese Patent Application No. 2006-350365 filed on Dec. 26, 2006, which are incorporated herein by reference.

FIELD OF THE INVENTION

The present invention relates to cosmetics containing a vitamin E derivative or a salt thereof. More specifically, the present invention relates to cosmetics that have no stickiness (in particular, the stickiness during drying after the application on the skin), are excellent in feeling in use, and which can contain with the variety and quantity of blendable oil components by the improvement of solubilizing ability and emulsifying ability.

BACKGROUND OF THE INVENTION

In recent years, various vitamin E derivatives have been synthesized, and they have been suggested as an antioxidant component and a moisture retaining component. Specific examples include vitamin E sulfuric acid esters (see unexamined patent publication (Kokai) No. 55-13214), polyethoxylated vitamin E (see unexamined patent publication (Kokai) No. 5-194474 and No. 11-35577), polyoxypropylene-polyoxyethylene vitamin E (see unexamined patent publication (Kohyo) No. 2002-517389), and polyoxypropylene-polyoxyethylene vitamin E with an added functional group (see unexamined patent publication (Kokai) No. 2003-277392). In the literature (Kokai No. 2003-277392), the compound was also suggested as a solubilizing agent, in which the vitamin E portion and the polyoxypropylene portion are hydrophobic groups and the polyoxyethylene portion is a hydrophilic group.

These conventional vitamin E derivatives are satisfactory in the functions as an antioxidant component or a moisture retaining component. However, the functions as a solubilizing agent or an emulsifier are still unsatisfactory, and they cannot realistically be used as a cosmetic raw material.

In addition, a lotion etc. that has no sticky feeling during drying after the application on the skin and is excellent in the feeling in use has been awaited.

DISCLOSURE OF THE INVENTION

Problem to be Solved by the Invention

The present inventors have diligently studied to solve the above-described conventional problems and to provide a vitamin E derivative having both the antioxidant activity and excellent moisture retaining property as well as much better emulsifying ability and solubilizing ability. As a result, the present inventors have found that vitamin E derivatives having hydrophobic butylene oxide groups and hydrophilic ethylene oxide groups, as the substituent, at position 6 of the chroman skeleton of vitamin E have equal to or a higher antioxidant activity and moisture retaining property than the above-described conventional vitamin E derivatives. In the surfactant performances such as the emulsifying ability and solubilizing ability, they also have a much higher activity and effect compared with the conventional vitamin E derivatives. In addition, the present inventors have found that they have a remarkably excellent effect, in a lotion etc., in reducing a sticky feeling on the skin (in particular, the sticky feeling during drying after the application on the skin), thus leading to completion of the present invention.

Means to Solve the Problem

That is, the present invention provides cosmetics containing a vitamin E derivative or a salt thereof that is represented by the following formula (I):

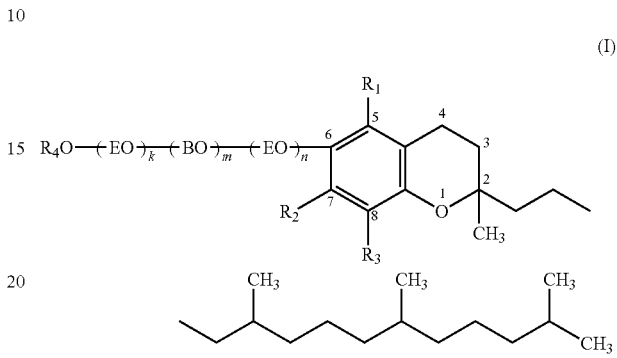

wherein $R_1$, $R_2$, and $R_3$ independently represent a hydrogen atom or a methyl group; $R_4$ represents a hydrogen atom, an alkanoyl group having carbon atoms 1 to 6, an alkyl group having 1 to 6 carbon atoms, an $SO_3H$ group, a $P(O)(OH)_2$ group, a $CH_2COOH$ group, or a $COCH_2CH(SO_3H)COOH$ group; EO represents an ethylene oxide group; BO represents a butylene oxide group; k and n independently represent any one of numbers 0 to 30 (however, k and n do not take 0 simultaneously); and m represents any one of numbers 1 to 30.

The present invention provides the above-described cosmetics in which $R_1$, $R_2$ and $R_3$ in formula (I) are methyl groups.

The present invention provides the above-described cosmetics in which $R_1$ and $R_3$ in formula (I) are methyl groups and $R_2$ is a hydrogen atom.

The present invention provides the above-described cosmetics in which $R_1$ in formula (I) is a hydrogen atom and $R_2$ and $R_3$ are methyl groups.

The present invention provides the above-described cosmetics in which $R_1$ and $R_2$ in formula (I) are hydrogen atoms and $R_3$ is a methyl group.

The present invention provides the above-described cosmetics in which $R_4$ in formula (I) is a hydrogen atom.

The present invention provides the above-described cosmetics in which $R_4$ in formula (I) represents an alkanoyl group having 1 to 6 carbon atoms, an alkyl group having 1 to 6 carbon atoms, an $SO_3H$ group, a $P(O)(OH)_2$ group, a $CH_2COOH$ group, or a $COCH_2CH(SO_3H)COOH$ group.

In addition, the present invention provides a solubilizing agent that comprises a vitamin E derivative represented by the above-described formula (I) or a salt thereof.

EFFECT OF THE INVENTION

According to the present invention, a sticky feeling on the skin (in particular, the sticky feeling during drying after the application on the skin) can be remarkably reduced while keeping a much better emulsifying ability and solubilizing ability as well as maintaining both antioxidant activity and an excellent moisture retaining property. In addition, the cosmetics excellent in the feeling in use such as a light fresh feeling, a permeation feeling, and affinity for the skin can be provided.

BEST MODE FOR CARRYING OUT THE INVENTION

Figure 1:
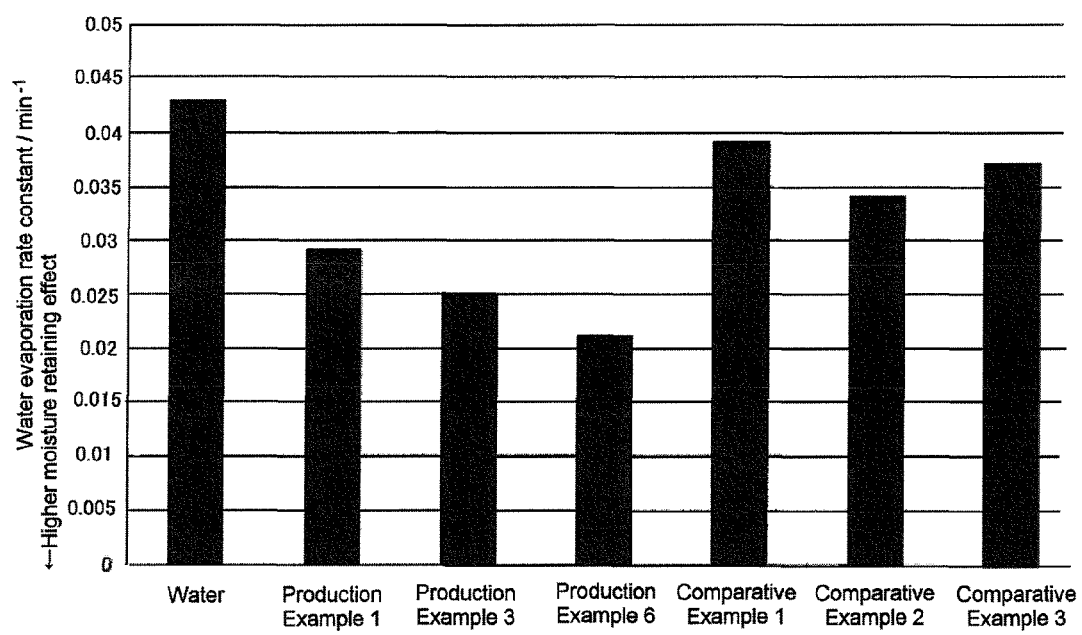
FIG. 1 is a graph that illustrates a comparison in the moisture retaining effect for Production Examples 1, 3, and 6 and Comparative Examples 1, 2, and 3, which were used in the examples.

Hereinafter, the present invention will be described in detail.

The cosmetics of the present invention comprise a vitamin E derivative represented by the following formula (I) or a salt thereof.

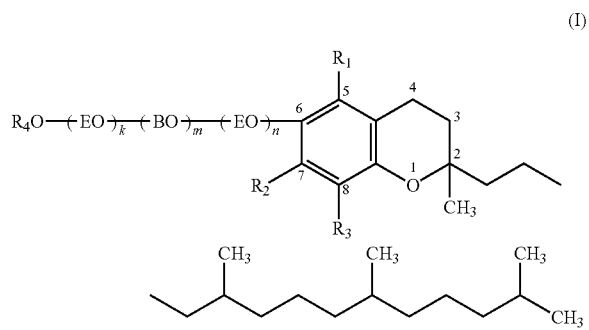

In the above-described formula (I), respective substituents are as follows. In the formula, EO represents an ethylene oxide group, and BO represents a butylene oxide group.

$R_1$, $R_2$, and $R_3$ independently represent a hydrogen atom or a methyl group. As the preferable combination of $R_1$, $R_2$, and $R_3$, a combination in which $R_1$, $R_2$ and $R_3$ are methyl groups (5,7,8-trimethyl form, the case in which the starting vitamin E is α-tocopherol); a combination in which $R_1$ and $R_3$ are methyl groups and $R_2$ is a hydrogen atom (5,8-dimethyl form, the case in which the starting vitamin E is β-tocopherol); a combination in which $R_1$ is a hydrogen atom and $R_2$ and $R_3$ are methyl groups (7,8-dimethyl form, the case in which the starting vitamin E is γ-tocopherol), and a combination in which $R_1$ and $R_2$ are hydrogen atoms and $R_3$ is a methyl group (8-methyl form, the case in which the starting vitamin E is δ-tocopherol) can be listed.

$R_4$ represents a hydrogen atom, an alkanoyl group having carbon atoms 1 to 6, an alkyl group having 1 to 6 carbon atoms, an $SO_3H$ group, a $P(O)(OH)_2$ group, a $CH_2COOH$ group, or a $COCH_2CH(SO_3H)COOH$ group.

The above-described alkanoyl group having 1 to 6 carbon atoms can be either linear or branched. Specific examples include an acetyl group, a propanoyl group, a butyryl group, an isobutyryl group, and a pivaloyl group. Among them, an acetyl group, a propanoyl group, and a pivaloyl group are preferable, and an acetyl group is more preferable from the standpoint of synthesis.

The above-described alkyl group having 1 to 6 carbon atoms can be either linear or branched. Specific examples include a methyl group, an ethyl group, a propyl group, a butyl group, an isobutyl group, a t-butyl group, a pentyl group, and a hexyl group. Among them, a methyl group, an ethyl group, a propyl group, and a butyl group are preferable, and a methyl group and an ethyl group are more preferable from the standpoint of synthesis.

An $SO_3H$ group, a $P(O)(OH)_2$ group, a $CH_2COOH$ group, or a $COCH_2CH(SO_3H)COOH$ group can form a salt with a base. There are no particular limitations as the base, if the toxicity is low and the antioxidant activity and moisture retaining property of the vitamin E derivative represented by the above-described formula (I) are not affected. Examples of such salts include alkali metal salts such as sodium salt, potassium salt, and lithium salt; alkaline earth metal salts such as calcium salt and magnesium salt; metal salts such as aluminum salt, iron salt, zinc salt, copper salt, nickel salt, and cobalt salt; and inorganic salts such as ammonium salt; organic amine salts such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, and tris(hydroxymethyl)aminomethane salt. However, the base is not limited to these examples. Among them, alkali metal salts, alkaline earth metal salts, and ammonium salt are preferable from the standpoint of synthesis. More preferable salts are sodium salt, potassium salt, ½ magnesium salt, ½ calcium salt, and ammonium salt, and sodium salt and ammonium salt are more preferable.

In the present invention from the standpoint of solubilizing ability, it is more preferable that $R_4$ in formula (I) represents an $SO_3H$ group or a $P(O)(OH)_2$ group and that they are in a salt form.

The symbols k and n respectively represent any one of numbers 0 to 30. They are preferably 0 to 25, and more preferably 0 to 20 (however, k and n do not take 0 simultaneously). The symbol m represents any one of numbers 1 to 30, preferably 1 to 10, and more preferably 1 to 5. The more preferable combination of k, m, and n is a combination in which k and n are respectively 0 to 20 (however, k and n do not take 0 simultaneously) and m is 1 to 5.

In the present invention, the compound represented by the above-described formula (I) has an asymmetric carbon in the molecule, and there are stereoisomers, namely, D-form and L-form. Each of them and an arbitrary mixture thereof are all included in the present invention.

When the compound represented by the above-described formula (I) is allowed to stand in the atmosphere, it may absorb water, adsorb water, or form a hydrate. Those cases are also included in the present invention.

In addition, the compound represented by the above-described formula (I) may absorb a certain other solvent and form a solvate. Those cases are also included in the present invention.

Vitamin E derivatives or salts thereof represented by the above-described formula (I) can be prepared, for example, by the method shown in the following production process chart.

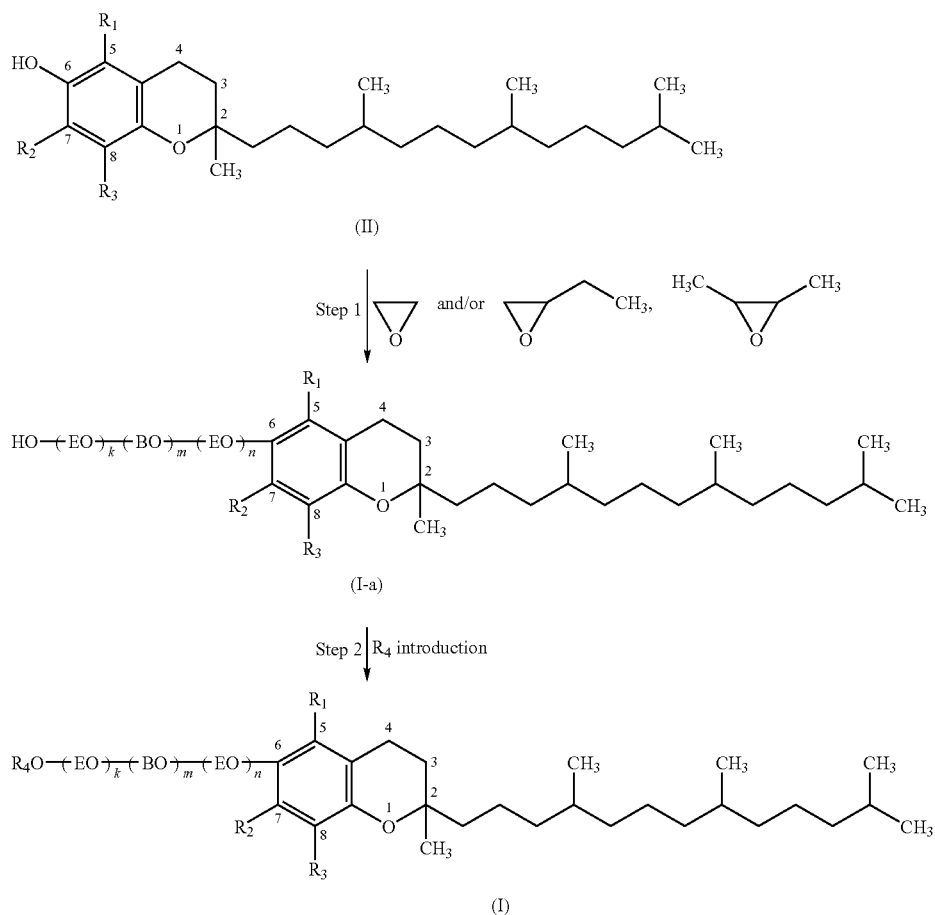

(Step 1) In step 1, a vitamin E derivative (alcohol form) represented by the above-described formula (I-a) is produced by the addition of ethylene oxide and/or butylene oxide, in the presence of a base catalyst, to a vitamin E represented by the above-described formula (II) [in the formula, $R_1$, $R_2$, and $R_3$ are respectively as defined for the above-described formula (I)].

As for vitamin E, either synthetic or natural vitamin Es can be used. Specific examples include α-tocopherol (5,7,8-trimethyl form) in which $R_1$, $R_2$, and $R_3$ are methyl groups in the above-described formula (II); β-tocopherol (5,8-dimethyl form) in which $R_1$ and $R_3$ are methyl groups and $R_2$ is a hydrogen atom; γ-tocopherol (7,8-dimethyl form) in which $R_2$ and $R_3$ are methyl groups and $R_1$ is a hydrogen atom; and δ-tocopherol (8-methyl form) in which $R_3$ is a hydrogen atom and $R_1$ and $R_2$ are methyl groups. In the present invention, commercial products can be preferably used, for example, a natural vitamin E (e.g., D-α-tocopherol, manufactured by Sigma-Aldrich Japan K.K.) and a synthetic vitamin E (e.g., DL-α-tocopherol, manufactured by Wako Pure Chemical Industries, Ltd.).

Examples of base catalysts (=alkaline catalysts) used in the addition reaction include alkali metal hydroxides such as sodium hydroxide and potassium hydroxide; alkali metal alkoxides such as sodium methoxide and potassium t-butoxide; metal hydrides such as sodium hydride and aluminum hydride; and quaternary ammonium hydroxides such as quaternary trimethylammonium hydroxides. Among them, potassium hydroxide, sodium hydroxide, etc. are preferably used because of easy handling.

The amount of a base catalyst varies depending upon reaction conditions and it is not limited in particular. In order to suppress side reactions, however, it is preferable to normally use 0.05 to 10 mass % with respect to vitamin E, which is the starting material, and it is more preferable to use 0.05 to 5 mass %.

The above-described addition reaction is conducted in the presence or absence of a solvent. The reaction in the presence of a solvent is more preferable from the standpoint of lowering the viscosity of the entire reaction system.

The solvent used is not limited in particular so far as it is not involved in the addition reaction. Examples include aromatic hydrocarbons such as toluene, xylene, and benzene; aliphatic hydrocarbons such as hexane, heptane, and octane; alicyclic hydrocarbons such as cyclohexane and cycloheptane; cyclic ethers such as tetrahydrofuran and dioxane; ethers such as diethyl ether, diisopropyl ether, ethylene glycol dimethyl ether, ethylene glycol diethyl ether, and diethylene glycol dimethyl ether; amides such as dimethylformamide and dimethylacetamide; and sulfoxides such as dimethylsulfoxide. However, the solvent is not limited to these examples. Among them, aromatic hydrocarbons, alicyclic hydrocarbons, cyclic ethers, ethers, etc. are preferably used.

Ethylene oxide and/or butylene oxide is normally injected. Butylene oxide preferably used in the present invention is 1,2-butylene oxide or 2,3-butylene oxide.

The injection temperature and reaction temperature (aging temperature) are normally from room temperature to 200° C., preferably from 50 to 200° C., and more preferably from 80 to 180° C. The reaction time (aging time) varies depending upon the reaction temperature; it is normally from 1 to 24 hours, preferably from 1 to 12 hours, and more preferably from 1 to 10 hours.

After the reaction, the reaction solution is cooled and the used base (catalyst) is neutralized with an acid. Examples of acids include mineral acids such as hydrochloric acid, sulfuric acid, nitric acid, hydrobromic acid, and phosphoric acid; and organic acids such as methanesulfonic acid, ethanesulfonic acid, acetic acid, and p-toluenesulfonic acid. However, the acid is not limited by these examples. Among them, hydrochloric acid, sulfuric acid, phosphoric acid, methanesulfonic acid, acetic acid, etc. are preferable, and more preferably, hydrochloric acid, phosphoric acid, methanesulfonic acid, acetic acid, etc. are used.

After neutralization, the desired product is obtained by a conventional treatment, for example, by adding water and a water-insoluble organic solvent, extracting, drying, and subsequently removing the organic solvent. When a generated salt is insoluble, the desired product can also be obtained by filtering the salt and removing the organic solvent. If necessary, the obtained desired compound, namely the compound represented by formula (I-a), can be purified by recrystallization, reprecipitation, or the separation by silica gel chromatography etc.

(Step 2) The compound obtained as described above and represented by formula (I-a) is a vitamin E derivative (alcohol form) in which $R_4$ is a hydrogen atom in formula (I) of the present invention.

The compound represented by the above-described formula (I-a) can be converted, by introducing the substituent $R_4$ (however, $R_4$ is other than a hydrogen atom) as desired, to a derivative in which an alkanoyl group having 1 to 6 carbon atoms, an alkyl group having 1 to 6 carbon atoms, an $SO_3H$ group, a $P(O)(OH)_2$ group, a $CH_2COOH$ group, a $COCH_2CH(SO_3H)COOH$ group, or a salt thereof is introduced. The introduction of the above-described substituent $R_4$ can be conducted according to the following methods (1) to (6). However, the method is not limited to these examples.

(1) An alkanoyl group having 1 to 6 carbon atoms is introduced by the reaction with an acid chloride or acid anhydride in the presence of a base and either in the presence or absence of a solvent.

Preferable examples of bases include organic bases such as triethylamine, diisopropylethylamine, pyridine, 4-dimethylaminopyridine, 1-methylpiperazine, 4-methylmorpholine, 1,4-dimethylpiperazine and 1-methylpyrrolidine.

The solvent is not limited in particular so far as it is not involved in the addition reaction. Examples include aromatic hydrocarbons such as toluene, xylene, and benzene; aliphatic hydrocarbons such as hexane, heptane, and octane; alicyclic hydrocarbons such as cyclohexane and cycloheptane; cyclic ethers such as tetrahydrofuran and dioxane; ethers such as diethyl ether, diisopropyl ether, ethylene glycol dimethyl ether, ethylene glycol diethyl ether, and diethylene glycol dimethyl ether; amides such as dimethylformamide and dimethylacetamide; and sulfoxides such as dimethylsulfoxide. However, the solvent is not limited to these examples. Among them, aromatic hydrocarbons, alicyclic hydrocarbons, cyclic ethers, ethers, etc. are preferably used.

Examples of acid chlorides include myristic acid chloride, palmitic acid chloride, and stearic acid chloride. Examples of acid anhydrides include maleic anhydride and acetic anhydride. However, the acid chloride and acid anhydride are not limited to these examples.

The reaction temperature varies depending upon acid chlorides and acid anhydrides; it is normally from –20° C. to 100° C., preferably from 0 to 100° C., and more preferably from 0 to 50° C.

The reaction time varies depending upon the reaction temperature; it is normally from 1 to 24 hours, preferably from 1 to 8 hours, and more preferably from 1 to 4 hours.

After the completion of the reaction, the desired product is obtained by a conventional treatment, for example, by adding water and a water-insoluble solvent, neutralizing as necessary, extracting, drying, and subsequently removing the solvent. When a generated salt is insoluble, the desired product can also be obtained by filtering the salt and removing the solvent. If necessary, the obtained desired compound can be purified by recrystallization, reprecipitation, or the separation by silica gel chromatography etc.

(2) An alkyl group having 1 to 6 carbon atoms is introduced by the reaction with an alkyl halide in the presence of a base and either in the presence or absence of a solvent.

Preferable examples of bases include alkali metal hydroxides such as sodium hydroxide and potassium hydroxide; alkali metal alkoxides such as sodium methoxide and potassium t-butoxide; metal hydrides such as sodium hydride and aluminum hydride; and quaternary ammonium hydroxides such as quaternary trimethylammonium hydroxides.

The solvent is not limited in particular so far as it is not involved in the addition reaction, and the solvents listed in the above-described (1) can be preferably used.

Examples of alkyl halides include methyl chloride and ethyl bromide. However, the alkyl halide is not limited to these examples.

The reaction temperature varies depending upon the alkyl halide; it is normally from –20° C. to 100° C., preferably from 0 to 100° C., and more preferably from 0 to 50° C.

The reaction time varies depending upon the reaction temperature; it is normally from 1 to 24 hours, preferably from 1 to 8 hours, and more preferably from 1 to 4 hours.

After the completion of the reaction, the desired product is obtained by a conventional treatment, for example, by adding water and a water-insoluble solvent, neutralizing as necessary, extracting, drying, and subsequently removing the solvent. When a generated salt is insoluble, the desired product can also be obtained by filtering the salt and removing the solvent. If necessary, the obtained desired compound can be purified by recrystallization, reprecipitation, or the separation by silica gel chromatography etc.

(3) An $SO_3H$ group is introduced by the reaction with sulfamic acid or sulfuric anhydride in the presence of urea and either in the presence or absence of a solvent.

The solvent is not limited in particular so far as it is not involved in the addition reaction, and the solvents listed in the above-described (1) can be suitably used.

The reaction temperature is normally from –20° C. to 100° C., preferably from 0 to 100° C., and more preferably from 0 to 50° C.

The reaction time varies depending upon the reaction temperature; it is normally from 1 to 24 hours, preferably from 1 to 8 hours, and more preferably from 1 to 4 hours.

After the completion of the reaction, the desired product is obtained by a conventional treatment, for example, by adding water and a water-insoluble solvent, neutralizing as necessary, extracting, drying, and subsequently removing the solvent. When a generated salt is insoluble, the desired product can also be obtained by filtering the salt and removing the solvent. If necessary, the obtained desired compound can be purified by recrystallization, reprecipitation, or the separation by silica gel chromatography etc.

(4) A $P(O)(OH)_2$ group is introduced by the reaction with diphosphorus pentaoxide (=phosphoric anhydride) or polyphosphoric acid either in the presence or absence of a solvent.

The solvent is not limited in particular so far as it is not involved in the addition reaction, and the solvents listed in the above-described (1) can be preferably used The reaction temperature varies depending upon whether diphosphorus pentaoxide is used or polyphosphoric acid is used; it is normally from room temperature to 200° C. and more preferably from room temperature to 150° C.

The reaction time varies depending upon the reaction temperature; it is normally from 1 to 24 hours, preferably from 1 to 8 hours, and more preferably from 1 to 4 hours.

After the completion of the reaction, the desired product is obtained by a conventional treatment, for example, by adding water and a water-insoluble solvent, neutralizing as necessary, extracting, drying, and subsequently removing the solvent. When a generated salt is insoluble, the desired product can also be obtained by filtering the salt and removing the solvent. If necessary, the obtained desired compound can be purified by recrystallization, reprecipitation, or the separation by silica gel chromatography etc.

(5) A $CH_2COOH$ group is introduced by the reaction with an alkyl monochloroacetate or alkyl monobromoacetate, in the presence of a base and either in the presence or absence of a solvent, and by the subsequent alkaline hydrolysis of the ester group.

Examples of bases include alkali metal hydroxides such as sodium hydroxide and potassium hydroxide; alkali metal alkoxides such as sodium methoxide, potassium methoxide, sodium ethoxide, potassium ethoxide, and potassium t-butoxide; and metal hydrides such as sodium hydride and aluminum hydride. Alkali metal alkoxides etc. are more preferably used.

The solvent is not limited in particular so far as it is not involved in the addition reaction. However, alcohols such as methanol, ethanol, propanol, butanol, t-butanol; cyclic ethers such as tetrahydrofuran and dioxane; and amides such as dimethylformamide and dimethylacetamide are preferable. The solvent, however, is not limited to these examples. Among them, alcohols such as methanol, ethanol, propanol, butanol, and t-butanol are more preferable.

The reaction temperature is not limited in particular; it is normally from room temperature to 100° C., preferably from room temperature to 80° C., and more preferably from room temperature to 50° C.

The reaction time varies depending upon the reaction temperature; it is normally from 1 to 24 hours, preferably from 1 to 12 hours, and more preferably from 1 to 8 hours.

The step in which the ester group is converted to a carboxylic acid or carboxylate salt by alkaline hydrolysis can be achieved with the use of an aqueous solution of an alkali metal hydroxide such as sodium hydroxide or potassium hydroxide.

After the reaction, the pH is adjusted to 2-4 with the use of an acid such as hydrochloric acid, sulfuric acid, or phosphoric acid. The carboxylic acid can be obtained by extracting with a solvent, drying, and removing the solvent.

As the extraction solvent, halogenated hydrocarbons such as methylene chloride and chloroform; aromatic hydrocarbons such as toluene, xylene, and benzene; esters such as ethyl acetate and methyl acetate; and ethers such as diethyl ether and diisopropyl ether are preferable. Among them, halogenated hydrocarbons are even more preferable.

The obtained desired compound can be used as it is in the succeeding step. If necessary, however, the compound can be purified by the conventional method such as recrystallization, reprecipitation, or the separation by silica gel chromatography etc.

(6) A $COCH_2CH(SO_3H)COOH$ group is introduced by the esterification reaction with maleic anhydride, in the presence of a catalytic amount of sodium acetate, and by the subsequent reaction with an aqueous solution of sodium sulfite.

The reaction temperature of esterification is normally from 50 to 200° C., preferably from 60 to 150° C., and more preferably from 70 to 100° C.

The reaction temperature with an aqueous solution of sodium sulfite is normally from 50 to 200° C., preferably from 60 to 150° C., and more preferably from 70 to 100° C.

The compounds obtained in the above-described (3), (4), (5) and (6) can be converted, as necessary, to a desired salt with the use of a base by the conventional method.

The moisture retaining property and antioxidant activity of the vitamin E derivatives of the present invention are comparable or higher compared with vitamin E or the conventional vitamin E derivatives proposed in patent literatures 1 to 5. However, the properties as a surfactant such as an emulsifier or solubilizing agent are better than the conventional vitamin E derivatives because of the introduction of hydrophobic butylene oxide groups. Accordingly, when a vitamin E derivative represented by the above-described formula (I) is blended into cosmetics, the variety and quantity range of blendable additive oil components can be increased. Specifically, the blending quantity of an oil component can be increased about 1.2 to 1.5 times compared with the case in which the conventional vitamin E derivative is used.

The excellent effect in that there is no sticky feeling (especially, no sticky feeling during drying after the application on the skin) is also noteworthy. This effect was long-felt needed in the past especially for a lotion etc. The product of the present invention can also be used, as an emulsifier or solubilizing agent, in pharmaceuticals, cosmetics, etc.

The blending quantity of a vitamin E derivative represented by the above-described formula (I) or a salt thereof in cosmetics is not limited in particular. However, when it is used as an emulsifier or solubilizing agent, a comparable blending quantity to that of a nonionic surfactant or ionic surfactant normally used as an emulsifier or solubilizing agent is preferable. Specifically, 0.01 to 5.0 mass % with respect to the total amount of a cosmetic is preferable, and more preferably it is 0.05 to 3.0 mass %.

When cosmetics are prepared with the use of a vitamin E derivative represented by the above-described formula (I) or a salt thereof, it is possible to arbitrarily blend other additive components, which are normally blendable into cosmetics, so far as the effect of the present invention is not undermined. Specific examples of such components include surfactants, oils, thickeners, moisturizers, UV absorbers, UV scatterers, drugs, perfumes, coloring agents, and stabilizing agents. However, the additive components are not limited to these examples.

Non-ionic surfactants include POF (=nolyoxyethylene) alkyl ethers such as POE cetyl ether (POE 7), POE cetyl ether (POE 10), POE oleyl ether (POE 6), POE oleyl ether (POE 10), POE stearyl ether (POE 6), POE oleyl ether (POE 8), POE lauryl ether (POE 5), POE hexyldecyl ether (POE 5), POE isostearyl ether (POE 5), POE octyldodecyl ether (POE 5), POE decyl pentadecyl ether (POE 10), POE behenyl ether (POE 10), POE decyl tetradecyl ether (POE 10) and POE cholesteryl ether (POE 10); POE alkylphenyl ethers such as POE nonylphenyl ether (POE 5), POE octylphenyl ether (POE 5) etc.; POE alkyl ether stearates such as POE stearyl ether stearate (POE 12), POE lauryl ether stearate (POE10), POE lauryl ether stearate (POE 15) and POE lauryl ether isostearate (POE 10); esters of ethylene glycol with fatty acid/polyethylene glycol such as ethylene glycol dilaurate/polyethylene glycol (POE 8), ethylene glycol dilaurate/polyethylene glycol (POE 12), ethylene glycol monostearate/polyethylene glycol (POE 5), ethylene glycol distearate/polyethylene glycol (POE 12) and ethylene glycol dioleate/polyethylene glycol (POE 12); polyethylene glycol fatty acid esters such as polyethylene glycol isostearate (POE 6), polyethylene glycol diisostearate (POE 12) and polyethylene glycol monooleate (POE 6); POE glyceryl fatty acid esters such as POE glyceryl isostearate (POE 5), POE glyceryl isostearate (POE 6) and POE glyceryl isostearate (POE 8); POE glyceryl tri-fatty acid esters such as POE glyceryl triisostearate (POE 20), POE glyceryl trioleate (POE 20) and POE glyceryl triisostearate (POE 7); POE trimethylolpropane tri-fatty acid esters such as POE trimethylolpropane trimyristate (POE 20), POE trimethylolpropane triisostearate (POE 20), POE trimethylolpropane triisostearate (POE 20), POE trimethylolpropane triisostearate (POE 25) and POE trimethylolpropane triisostearate (POE 30); POE-hydrogenated castor oils and their derivatives such as POE-hydrogenated castor oil (POE 20), POE castor oil (POE 20), POE-hydrogenated castor oil laurate (POE 20), POE-hydrogenated castor oil isostearate (POE 20), POE-hydrogenated castor oil isostearate (POE 30), POE-hydrogenated castor oil triisostearate (POE 40) and POE-hydrogenated castor oil triisostearate (POE 50); POE glycerin monostearate (POE 5); sorbitan-monoisostearate; glycerin monostearate (Self-emulsifying); diglyceryl monostearate; and cetostearyl glucoside.

Ionic surfactants include alkyl phosphate such as sodium lauryl phosphate and lauryl phosphate; POE alkyl ether phosphates such as POE (1) lauryl ether phosphate and sodium laurel phosphate; N-acyl taurine salts such as sodium N-cocoyl N-methyltaurate sodium N-lauroyl N-methyltaurate, sodium N-myristoyl N-methyltaurate, sodium N-palmitoyl N-methyltaurate and sodium N-stearoyl N-methyltaurate; alkyl sulfates such as ammonium lauryl sulfate, potassium lauryl sulfate, sodium lauryl sulfate, triethanolamine lauryl sulfate, sodium myristyl sulfate and sodium cetyl sulfate; POE alkyl ether sulfate such as sodium POE (3 mol) alkyl ($C_{12-15}$) ether sulfate, triethanolamine POE (3 mol) alkyl ($C_{12-15}$) ether sulfate, ammonium POE (2 mol) lauryl ether sulfate, sodium POE (2 mol) lauryl ether sulfate, triethanolamine POE (2 mol) lauryl ether sulfate, sodium POE (3 mol) lauryl ether sulfate and sodium POE (2 mol) lauryl ether sulfate; and sulfonates such as sodium lauryl sulfoacetate, sodium tetradecene sulfonate and dioctyl sodium sulfosuccinate.

Ampholytic surfactants include betaine acetate-type ampholytic surfactants such as lauryl dimethylamino acetic acid betaine, coconut oil fatty acid amide propyl dimethylamino acetic acid betaine and coconut oil fatty acid amide propyl dimethylamino acetic acid betaine; and imidazoline-type ampholytic surfactants such as sodium N-coconut oil fatty acid acyl-N-carboxymethyl-N-hydroxyethyl ethylenediamine.

Oils include ester oils such as tripropylene glycol dineopentanoate, isodecyl benzoate, propylene glycol dicaprylate, isononyl isononanoate, cetyl 2-ethylhexanoate, glyceryl tri-2-ethylhexanoate, pentaerythritol tetra-2-ethylhexanoate, di-2-ethylhexyl succinate and 2-ethylhexyl 2-ethylhexanoate; hydrocarbon oils such as liquid paraffin, ozocerite, squalane, pristane, paraffin, ceresin, squalene, vaseline, microcrystalline wax, polyethylene wax and Fisher-Tropsch wax; silicone oils such as chain polysiloxanes (e.g. dimethylpolysiloxane, methylphenyl polysiloxane, diphenyl polysiloxane etc.), cyclic polysiloxanes (e.g. decamethylcyclopentasiloxane, dodecamethylcyclohexasiloxane etc.), silicone resins having a three-dimensional network structure, silicone rubbers having an average molecular weight of 200,000 or more and various modified polysiloxanes (e.g. amino-modified polysiloxane, polyether-modified polysiloxane, alkyl-modified polysiloxane, fluorine-modified polysiloxane etc.); waxes such as bees wax, candelilla wax, carnauba wax, lanolin, liquid lanolin and jojoba wax; higher alcohols such as hexyl alcohol, octyl alcohol, cetyl alcohol, stearil alcohol, seryl alcohol, behenyl alcohol, triacontyl alcohol, selachyl alcohol and batyl alcohol; and higher fatty acids such as lauric acid, myristic acid, palmitic acid and behenic acid.

Thickeners include acrylamide thickeners such as vinylpyrrolidone/2-acrylamide-2-methylpropane sulfonic acid copolymer, dimethyl acrylamide/2-acrylamide-2-methylpropane sulfonic acid copolymer, amide acrylate/2-acrylamide-2-methylpropane sulfonic acid copolymer, a mixture of polyacrylic acid and sodium polyacrylate, sodium acrylate/2-acrylamide-2-methylpropane sulfonic acid copolymer, ammonium polyacrylate, polyacrylamide/ammonium polyacrylate copolymer and acrylamide/sodium acrylate copolymer; acrylic thickeners such as carboxy vinyl polymer and alkyl-modified carboxy vinyl polymer; water-soluble polymers such as carrageenan, pectine, mannan, curdlan, chondroitin sulfate, starch, glycogen, gum arabic, sodium hyaluronate, gum tragacanth, xanthan gum, mucoitin sulfuric acid, hydroxyethyl guar gum, carboxymethyl guar gum, guar gum, dextran, kerato sulfuric acid, locust bean gum, succinoglycan, chitin, chitosan, carboxymethyl chitin and agar.

Moisturizers include polyethylene glycol, glycerin, diglycerin, 1,3-butylene glycol, erythritol, sorbitol, xylitol, maltitol, 1,2-pentanediol and hexylene glycol.

UV absorbers include, for example, cinnamic acid type UV absorbers such as para-aminobenzoic acid, octyl-p-methoxy cinnamate (2-ethylhexyl-p-methoxy cinnamate), glyceryl-mono-2-ethyl hexanoyl-di-p-methoxy cinnamate and methyl bis(trimethylsiloxy) silyl isopentyl trimethoxy cinnamate; 2,2'-hydroxy-5-methylphenylbenzotriazole; 2-(2'-hydroxy-5'-t-octylphenyl)-benzotriazole; 2-(2'-hydroxy-5'-methylphenyl)-benzotriazole, 4-methoxy-4'-t-butyl dibenzoylmethane; 5-(3,3-dimethyl-2-norbornilidene)-3-pentane-2-on; bis-ethylhexyloxyphenol methoxyphenyl triazine; 2,4,6-tris[4-(2-ethylhexyloxycarbonyl) anilino]-1,3,5-triazine; and dimorpholino pyridazinone.

UV scatterers include, for example, powders such as fine particulate titanium oxide having an average particle size of 10-100 nm, fine particulate zinc oxide, fine particulate iron oxide and fine particulate cerium oxide.

Drugs include L-ascorbic acid; L-ascorbic acid monoalkyl esters such as L-ascorbic acid monostearate, L-ascorbic acid monopalmitate and L-ascorbic acid monooleate; L-ascorbic acid monoesters such as L-ascorbic acid monophosphate ester and L-ascorbic acid-2-sulfate ester; L-ascorbic acid dialkyl esters such as L-ascorbic acid distearate, L-ascorbic acid dipalmitate and L-ascorbic acid dioleate; L-ascorbic acid trialkyl esters such as L-ascorbic acid tristearate, L-ascorbic acid tripalmitate and L-ascorbic acid trioleate; L-ascorbic acid triesters such as L-ascorbic acid triphosphate ester; L-ascorbic acid glucosides such as L-ascorbic acid-2-glucoside; tranexamic acid dimers (e.g. trans-4-(trans-aminomethyl cyclohexane carbonyl)aminomethyl cyclohexane carboxylic acid hydrochloride, etc.), esters of tranexamic acid and hydroquinone (e.g. 4-(trans-aminomethyl cyclohexane carboxylic acid) 4'-hydroxyphenyl ester, etc.), esters of tranexamic acid and gentisic acid (e.g. 2-(trans-4-aminomethyl cyclohexyl carbonyloxy)-5-hydroxy benzoic acid, etc.), amides of tranexamic acid (e.g. trans-4-aminomethyl cyclohexane carboxylic acid methylamide, trans-4-(p-methoxybenzoyl)aminomethyl cyclohexane carboxylic acid, trans-4-guanidinomethyl cyclohexane carboxylic acid, etc.), salts of tranexamic acid or derivatives; alkoxy salicylic acids such as 3-methoxy salicylic acid, 3-ethoxy salicylic acid, 4-methoxy salicylic acid, 4-ethoxy salicylic acid, 4-propoxy salicylic acid, 4-isopropoxy salicylic acid, 4-butoxy salicylic acid, 5-methoxy salicylic acid, 5-ethoxy salicylic acid, 5-propoxy salicylic acid and salts thereof; vitamins such as vitamin A, vitamin A derivatives (e.g. vitamin A palmitate, vitamin A acetate, etc.), vitamin B group (e.g. vitamin $B_6$ hydrochloride, vitamin $B_6$ tripalmitate, vitamin $B_6$ dioctanoate, vitamin $B_2$ and its derivatives, vitamin $B_{12}$, vitamin $B_{15}$ and its derivatives, etc.), vitamin D group, vitamin H, pantothenic acid and pantethine; γ-orizanol; allantoin; glycyrrhizic acid (glycyrrhizinate); glycyrrhetic acid; stearyl glycyrrhetinate; hinokitiol; bisabolol; eucalyptone; thymol; inositol; saponins such as saikosaponin, carrot saponin, loofah saponin and soapberry saponin; various drugs such as pantothenyl ethyl ether, arbutin and cepharanthine; plant extracts such as dock, *sophora angustifolia, nuphar*, orange, sage, yarrow, mall, *Swertia japonica*, thyme, *angelica acutiloba*, spruce, birch, field horsetail, loofah, horse chestnut, *saxifrage sarmentosa, scutellaria baicalensis, arnica*, lily, *artemisia*, peony, aloe, gardenia and cherry leaf; and β-carotene.

In addition, various perfumes and lower alcohols such as ethanol can be blended. Furthermore, antioxidants such as butylhydroxytoluene, δ-tocopherol, and phytin; and preservatives such as benzoic acid, salicylic acid, sorbic acid, paraoxybenzoic acid alkyl ester, phenoxyethanol, hexachlorophene, and ε-polylysine can be blended as the stabilizing agent. Organic and inorganic acids such as citric acid, lactic acid, and hexametaphosphoric acid; and salts thereof can also be blended.

The cosmetics containing a vitamin E derivative represented by the above-described formula (I) of the present invention or a salt thereof can be especially preferably used in a lotion, milky lotion, essence, skin cream, etc. They are also suitably used in a hair treatment agent, hair styling agent, etc.

DESCRIPTION OF THE PREFERRED EMBODIMENT

Examples

Hereinafter, the present invention will be described in further detail with reference to examples. However, the present invention is not limited by the following examples. The blending quantities are all expressed in mass %.

Production Example 1

Potassium salt of DL-α-tocopherol ethylene oxide/butylene oxide/ethylene oxide addition product sulfuric acid ester [in the above-described formula (I), k=5, m=2, n=1, block, $R_1$, $R_2$, $R_3$=$CH_3$, $R_4$=potassium salt of $SO_3$]

(i) Synthesis of DL-α-tocopherol ethylene oxide/butylene oxide/ethylene oxide addition product (k=5, m=2, n=1, block)

Into an autoclave, 205.1 g of DL-α-tocopherol and 0.61 g of potassium hydroxide (0.30 mass % with respect to DL-α-tocopherol), as the base catalyst, were loaded. After the inside of the vessel was replaced with nitrogen gas, the temperature was increased to 100-110° C., and the dehydration was conducted for 0.5 hours. Then, the temperature was increased to 130-140° C., 21.0 g of ethylene oxide was injected over the course of 0.5 hours, and aging was carried out for 4.0 hours. Subsequently, 68.6 g of butylene oxide was injected at 140-150° C. over the course of 0.5 hours, and then aging was carried out for 2.0 hours. After the completion of aging, the cooling was carried out, and 366.2 g of the desired product was obtained.

Infrared absorption spectrum ν $cm^{-1}$ (neat) 2922; 2868, 1462, 1414, 1378, 1257, 1091, 988, 942, 920, 910, 875, 853.

(ii) Synthesis of potassium salt of DL-α-tocopherol ethylene oxide/butylene oxide/ethylene oxide addition product sulfuric acid ester [in the above-described formula (I), k=5, m=2, n=1, block, $R_1$, $R_2$, $R_3$=$CH_3$, $R_4$=potassium salt of $SO_3$]

Into a four-neck flask, 366.2 g of the DL-α-tocopherol ethylene oxide/butylene oxide/ethylene oxide addition product (k=5, m=2, n=1, block), which was synthesized in the above-described (i), was added, and the temperature was increased to 100-110° C. To this was added 0.22 g of monosodium phosphate, and then 2.17 g of urea and 41.2 g of sulfamic acid were added while the same temperature was being maintained. At the same temperature, aging was carried out for 6 hours while the sulfamic acid was being added. Then the cooling was carried out, 500 g of methanol and 6.0 g of aqueous ammonia were added, and the filtration was conducted. To the obtained solution, 20.8 g of potassium hydroxide was added, the methanol was removed by heating, 240 g of ethanol was added, and the filtration was conducted. Excess ethanol was removed by heating the filtrate, and 370 g of the desired product (10% residual ethanol is contained) was obtained.

Infrared absorption spectrum ν $cm^{-1}$ (neat): 2926, 2870, 1461, 1415, 1377, 1255, 1090, 1025, 948, 922, 861.

Under reduced pressure, 5 g of the product was dried at 80° C. for 5 hours, and 4.5 g of the desired product (dry product) was obtained.

Infrared absorption spectrum ν $cm^{-1}$ (neat): 2922, 2867, 1461, 1414, 1377, 1253, 1090, 1027, 996, 948, 924, 899, 856.

$^1$H-NMR: 0.83-0.87 (12.5H), 0.92-1.00 (5.2H), 1.05-1.80 (31.7H), 2.07 (3H), 2.13 (3H), 2.17 (3H), 2.56 (2.6H), 3.59-3.73 (71.3H).

Structural Analysis Results Based on Multiple-Collision Induced Dissociation ($MS^n$) Mass Spectrum (Electrospray (Negative Ion Detection), Helium Collision Gas)

The product was confirmed, from the following data, to be the potassium salt of DL-α-tocopherol ethylene oxide/butylene oxide/ethylene oxide addition product sulfuric acid ester [in the above-described formula (I), k=5, m=2, n=1, block, $R_1$, $R_2$, $R_3$=$CH_3$, $R_4$=potassium salt of $SO_3$]

(1) m/z 917.60: ion obtained by potassium removal, $C_{49}H_{89}O_{13}S_1$

Multiple-collision induced dissociation ($MS^n$) mass spectrum (electrospray (negative ion detection), helium collision gas)

MS/MS
(2) m/z 487: (1)—430 (tocopherol)
(3) m/z 443: (2)—44 (EO)
MS/MS/MS
(4) m/z 371: (3)—72 (BO)
MS/MS/MS/MS (5) m/z 299: (4)—72 (BO)
MS/MS/MS/MS/MS
(6) m/z 255: (5)—44 (EO)
(7) m/z 211: (5)—88 (2EO).

Production Example 2

DL-α-tocopherol ethylene oxide/butylene oxide/ethylene oxide addition product [in the above-described formula (I), k=16, m=2, n=0, $R_1$, $R_2$, $R_3$=$CH_3$, $R_4$=H]

Into an autoclave, 134.6 g of DL-α-tocopherol and 0.40 g of potassium hydroxide, as the base catalyst, were loaded. After the inside of the vessel was replaced with nitrogen gas, the temperature was increased to 100-110° C., and the dehydration was conducted for 0.5 hours. Then the temperature was increased to 140-150° C., and 45.0 g of 1,2-butylene oxide was injected over the course of 0.5 hours. While the same temperature was being maintained, aging was carried out for 4.0 hours. Subsequently, 220.0 g of ethylene oxide was injected over the course of 2.5 hours, and then aging was carried out for 2.0 hours. After the completion of aging, the cooling was carried out, and the product was neutralized with phosphoric acid aqueous solution and purified. The formed salt was filtered, and 347.2 g of the desired product (yield: 86.8%) was obtained.

$^1$H-NMR: 0.83-0.87 (13.2H), 0.92-1.00 (5.7H), 1.05-1.80 (31.2H), 2.07 (3H), 2.13 (3H), 2.17 (3H), 2.56 (1.8H), 3.59-3.73 (29.9H).

Structural Analysis Results Based on Multiple-Collision Induced Dissociation ($MS^n$) Mass Spectrum (Electrospray (Negative Ion Detection), Helium Collision Gas)

The product was confirmed, from the following data, to be DL-α-tocopherol ethylene oxide/butylene oxide/ethylene oxide addition product [in the above-described formula (I), m=2, n=0, $R_1$, $R_2$, $R_3$=$CH_3$, $R_4$=H].

Mass spectrum (electrospray (positive ion detection))
(1) m/z 1296.95: ammonium addition ion, $C_{69}H_{130}O_{20}$+$NH_4$ (ammonia is derived from the mobile phase solvent) (m/z: mass/charge ratio)
Collision-induced dissociation (MS/MS) mass spectrum (electrospray (positive ion detection), helium collision gas)
MS/MS
(2) m/z 1261: (1)-18 ($H_2O$)
(3) m/z 1217, 1173, 1129, 1085, 1041, 997, 953, 909, 865, 821, 777, 733, 689, 645, 601, 557: (2)—44×N(N=1-16, EO)
(3) m/z 485: (2)—44×16-72 (BO)
(4) m/z 1279: (1)—18 ($NH_4$)
(5) m/z 849: (4)—430 (tocopherol)
(6) m/z 777: (5)—72 (BO)
(7) m/z 705: (6)—72 (BO)
(8) m/z 661, 617, 573, 529, 485, 441, 397: (2)—44×N(N=1-7, EO).

Production Example 3

DL-α-tocopherol ethylene oxide/butylene oxide/ethylene oxide addition product [in the above-described formula (I), k=14, m=2, n=14, block, $R_1$, $R_2$, $R_3$=$CH_3$, $R_4$=H]

Into an autoclave, 60.5 g of DL-α-tocopherol (manufactured by Riken Vitamin Co., Ltd.) and 0.24 g of potassium hydroxide, as the base catalyst, were loaded. After the inside of the vessel was replaced with nitrogen gas, the temperature was increased to 100-110° C., and the dehydration was conducted for 0.5 hours. Then, the temperature was increased to 130-140° C., and 86.5 g of ethylene oxide (manufactured by Nippon Shokubai Co., Ltd.) was injected over the course of 1.5 hours. While the same temperature was being maintained, aging was carried out for 1.0 hour. Subsequently, 16.3 g of 1,2-butylene oxide (manufactured by Tokyo Chemical Industry Co., Ltd.) was injected over the course of 0.5 hours, and then aging was carried out for 2.0 hours. Lastly, 86.3 g of ethylene oxide was injected over the course of 1.0 hour, and then aging was carried out for 1.0 hour. After the completion of aging, the cooling was carried out, the product was neutralized with phosphoric acid aqueous solution and purified, the formed salt was filtered, and 210.0 g (yield: 84.0%) of the desired product was obtained.

Production Example 4

DL-α-tocopherol ethylene oxide/butylene oxide/ethylene oxide addition product [in the above-described formula (I), k 6, m=2, n=3, block, $R_1$, $R_2$, $R_3$=$CH_3$, $R_4$=H]

Into an autoclave, 177.2 g of DL-α-tocopherol and 0.53 g (0.30 mass % with respect to DL-α-tocopherol) of potassium hydroxide, as the alkaline catalyst, were loaded. After the inside of the vessel was replaced with nitrogen gas, the temperature was increased to 100-110° C., and the dehydration was conducted for 0.5 hours. Then, the temperature was increased to 130-140° C., 54.3 g of ethylene oxide was injected over the course of 0.5 hours, and then aging was carried out for 2.0 hours. Subsequently, 59.3 g of butylene oxide was injected at 140-150° C. over the course of 0.5 hours, and then aging was carried out for 4.0 hours. Lastly, 108.6 g of ethylene oxide was injected at 130-140° C. over the course of 1.0 hour, and then aging was carried out for 2.0 hours. After the completion of aging, the cooling was carried out, and 360.0 g of the desired product was obtained.

Infrared absorption spectrum v $cm^{-1}$ (neat): 2926, 2868, 1460, 1377, 1350, 1252, 996, 945, 914.

Production Example 5

DL-α-tocopherol ethylene oxide/butylene oxide/ethylene oxide addition product [in the above-described formula (I), k=16, m 4, n=0, $R_1$, $R_2$, $R_3$ $CH_3$, $R_4$=H]

Into an autoclave, 94.5 g of DL-α-tocopherol and 0.38 g of potassium hydroxide, as the base catalyst, were loaded. After the inside of the vessel was replaced with nitrogen gas, the temperature was increased to 100-110° C., and the dehydration was conducted for 0.5 hours. Then, the temperature was increased to 130-140° C., and 50.9 g of 1,2-butylene oxide was injected over the course of 1.5 hours. While the same temperature was being maintained, aging was carried out for 2.0 hours. Subsequently, 154.5 g of ethylene oxide was injected over the course of 1.5 hours, and then aging was carried out for 2.0 hours. After the completion of aging, the cooling was carried out, and the product was neutralized with phosphoric acid aqueous solution and purified. The formed salt was filtered, and 246.5 g (yield: 82.1%) of the desired product was obtained.

Production Example 6

DL-α-tocopherol ethylene oxide/butylene oxide/ethylene oxide addition product [in the above-described formula (I), k=5, m=2, n=1, block, $R_1$, $R_2$, $R_3$=$CH_3$, $R_4$=H]

Into an autoclave, 205.1 g of DL-α-tocopherol and 0.61 g (0.30 mass % with respect to DL-α-tocopherol) of potassium hydroxide, as the alkaline catalyst, were loaded. After the inside of the vessel was replaced with nitrogen gas, the temperature was increased to 100-110° C., and the dehydration was conducted for 0.5 hours. Then, the temperature was increased to 130-140° C., 21.0 g of ethylene oxide was injected over the course of 0.5 hours, and then aging was carried out for 2.0 hours. Subsequently, 68.6 g of butylene oxide was injected at 140-150° C. over the course of 0.5 hours, and then aging was carried out for 4.0 hours. Lastly, 104.8 g of ethylene oxide was injected at 130-140° C. over the course of 1.5 hours, and then aging was carried out for 2.0 hours. After the completion of aging, the cooling was carried out, and 366.2 g of the desired product was obtained.

Infrared absorption spectrum ν $cm^{-1}$ (neat): 2922, 2868, 1462, 1414, 1378, 1257, 1091, 988, 942, 920, 910, 875, 853.

Production Example 7

DL-α-tocopherol ethylene oxide/butylene oxide/ethylene oxide addition product [in the above-described formula (I), k=16, m=2, n=14, $R_1$, $R_2$, $R_3$=$CH_3$, $R_4$=H]

Into an autoclave, 83.3 g of DL-α-tocopherol and 0.22 g of potassium hydroxide, as the base catalyst, were loaded. After the inside of the vessel was replaced with nitrogen gas, the temperature was increased to 100-110° C., and the dehydration was conducted for 0.5 hours. Then, the temperature was increased to 130-140° C., and 79.8 g of ethylene oxide was injected over the course of 1.0 hour. While the same temperature was being maintained, aging was carried out for 2.0 hours. Subsequently, 15.0 g of 1,2-butylene oxide was injected over the course of 0.5 hours, and then aging was carried out for 1.5 hours. Lastly, 91.2 g of ethylene oxide was injected over the course of 1.5 hours, and then aging was carried out for 2.0 hours. After the completion of aging, the cooling was carried out, and the product was neutralized with phosphoric acid aqueous solution and purified. The formed salt was filtered, and 238.0 g (yield: 88.3%) of the desired product was obtained.

Production Example 8

Sodium salt of DL-α-tocopherol ethylene oxide/butylene oxide/ethylene oxide addition product sulfuric acid ester [in the above-described formula (I), k=14, m=2, n=14, $R_1$, $R_2$, $R_3$=$CH_3$, $R_4$=$SO_3Na$]

Into a four-neck flask, 360.0 g of the DL-α-tocopherol ethylene oxide/butylene oxide/ethylene oxide addition product (k=14, m=2, n=14), which was synthesized in Production Example 3, was placed, and the temperature was increased to 100-110° C. To this was added 0.19 g of monosodium phosphate, and 1.86 g of urea and 37.2 g of sulfamic acid were added while the same temperature was being maintained. At the same temperature, aging was carried out for 6 hours while the sulfamic acid was being added. Then the cooling was carried out, 500 g of methanol and 6.0 g of aqueous ammonia were added, and the filtration was conducted. To the obtained solution, 19.9 g of potassium hydroxide was added, the methanol was removed by heating, 240 g of ethanol was added, and the filtration was conducted. Excess ethanol was removed by heating the filtrate, and 354 g (10% residual ethanol is contained) of the desired product was obtained.

Infrared absorption spectrum ν $cm^{-1}$ (neat): 2923, 2869, 1456, 1417, 1376, 1254, 1089, 1032, 949, 927, 893, 879, 853.

Production Example 9

DL-α-tocopherol ethylene oxide/butylene oxide/ethylene oxide addition product [in the above-described formula (I), k 8, m=2, n=2, $R_1$, $R_2$, $R_3$=$CH_3$, $R_4$=H]

Into an autoclave, 142.9 g of DL-α-tocopherol and 0.57 g of potassium hydroxide, as the base catalyst, were loaded. After the inside of the vessel was replaced with nitrogen gas, the temperature was increased to 100-110° C., and the dehydration was conducted for 0.5 hours. Then, the temperature was increased to 130-140° C., and 29.2 g of ethylene oxide was injected over the course of 15 minutes. While the same temperature was being maintained, aging was carried out for 1.0 hour. Subsequently, 38.5 g of 1,2-butylene oxide was injected over the course of 0.5 hours, and then aging was carried out for 3.0 hours. Lastly, 117.2 g of ethylene oxide was injected over the course of 1.5 hours, and then aging was carried out for 2.0 hours. After the completion of aging, the cooling was carried out, the product was neutralized with phosphoric acid aqueous solution and purified. The formed salt was filtered, and 245.0 g (yield: 74.6%) of the desired product was obtained.

Production Example 10

DL-α-tocopherol ethylene oxide/butylene oxide/ethylene oxide addition product [in the above-described formula (I), k=10, m=2, n=2, $R_1$, $R_2$, $R_3$=$CH_3$, $R_4$=H]

Into an autoclave, 142.7 g of DL-α-tocopherol and 0.57 g of potassium hydroxide, as the base catalyst, were loaded. After the inside of the vessel was replaced with nitrogen gas, the temperature was increased to 100-110° C., and the dehydration was conducted for 0.5 hours. Then, the temperature was increased to 130-140° C., and 29.1 g of ethylene oxide was injected over the course of 15 minutes. While the same temperature was being maintained, aging was carried out for 1.0 hour. Subsequently, 38.4 g of 1,2-butylene oxide was injected over the course of 0.5 hours, and then aging was carried out for 3.0 hours. Lastly, 146.2 g of ethylene oxide was injected over the course of 1.0 hour, and then aging was carried out for 2.0 hours. After the completion of aging, the cooling was carried out, and the product was neutralized with phosphoric acid aqueous solution and purified. The formed salt was filtered, and 276.0 g (yield: 77.3%) of the desired product was obtained.

Production Example 11

DL-α-tocopherol ethylene oxide/butylene oxide/ethylene oxide addition product [in the above-described formula (I), k=12, m=2, n=3, $R_1$, $R_2$, $R_3$=$CH_3$, $R_4$=H]

Into an autoclave, 135.4 g of DL-α-tocopherol and 0.54 g of potassium hydroxide, as the base catalyst, were loaded.

After the inside of the vessel was replaced with nitrogen gas, the temperature was increased to 100-110° C., and the dehydration was conducted for 0.5 hours. Then, the temperature was increased to 130-140° C., and 27.7 g of ethylene oxide was injected over the course of 15 minutes. While the same temperature was being maintained, aging was carried out for 1.0 hour. Subsequently, 36.5 g of 1,2-butylene oxide was injected over the course of 0.5 hours, and then aging was carried out for 3.0 hours. Lastly, 167.2 g of ethylene oxide was injected over the course of 1.5 hours, and then aging was carried out for 2.0 hours. After the completion of aging, the cooling was carried out, and the product was neutralized with phosphoric acid aqueous solution and purified. The formed salt was filtered, and 303.0 g (yield: 82.5%) of the desired product was obtained.

Production Example 12

DL-α-tocopherol ethylene oxide/butylene oxide/ethylene oxide addition product [in the above-described formula (I), k=14, m=2, n=2, $R_1$, $R_2$, $R_3$=$CH_3$, $R_4$=H]

Into an autoclave, 119.5 g of DL-α-tocopherol and 0.48 g of potassium hydroxide, as the base catalyst, were loaded. After the inside of the vessel was replaced with nitrogen gas, the temperature was increased to 100-110° C., and the dehydration was conducted for 0.5 hours. Then, the temperature was increased to 130-140° C., 24.4 g of ethylene oxide was injected over the course of 15 minutes. While the same temperature was being maintained, aging was carried out for 1.0 hour. Subsequently, 32.1 g of 1,2-butylene oxide was injected over the course of 0.5 hours, and then aging was carried out for 3.0 hours. Lastly, 171.9 g of ethylene oxide was injected over the course of 1.5 hours, and then aging was carried out for 2.0 hours. After the completion of aging, the cooling was carried out, and the product was neutralized with phosphoric acid aqueous solution and purified. The formed salt was filtered, and 265.6 g (yield: 76.2%) of the desired product was obtained.

Production Example 13

Potassium salt of DL-α-tocopherol ethylene oxide/butylene oxide/ethylene oxide addition product sulfuric acid ester [in the above-described formula (I), k=14, m=2, n=0, $R_1$, $R_2$, $R_3$=$CH_3$, $R_4$=potassium salt of $SO_3$]

Into an autoclave, 111.0 g of DL-α-tocopherol and 0.44 g of potassium hydroxide, as the base catalyst, were loaded. After the inside of the vessel was replaced with nitrogen gas, the temperature was increased to 100-110° C., and the dehydration was conducted for 0.5 hours. Then, the temperature was increased to 130-140° C., 29.9 g of 1,2-butylene oxide was injected over the course of 0.5 hours, and then aging was carried out for 3.0 hours. Subsequently, 158.7 g of ethylene oxide was injected over the course of 1.5 hours, and then aging was carried out for 2.0 hours.

After the completion of aging, the cooling was carried out. Into a four-neck flask, 280.0 g of the synthesized DL-α-tocopherol ethylene oxide/butylene oxide/ethylene oxide (k=14, m=2, n=0) was taken and loaded, the temperature was increased to 100-110° C., and the dehydration was conducted. While the same temperature was being maintained, 4.41 g of urea and 30.9 g of sulfamic acid were added in installments. At the same temperature, aging was carried out for 3 hours, and then the cooling was carried out. After 260 g of methanol and 4.3 g of aqueous ammonia were added, the filtration was conducted. To the obtained solution, 13.8 g of potassium hydroxide was added, the methanol was removed by heating, and 230 g (yield: 75.8%) of the desired product was obtained.

Production Example 14

Potassium salt of DL-α-tocopherol ethylene oxide/butylene oxide/ethylene oxide addition product sulfuric phosphoric acid ester [in the above-described formula (I), k=14, m=2, n=2, $R_1$, $R_2$, $R_3$=$CH_3$, $R_4$=potassium salt of $P(O)(OH)_2$]

Into an autoclave, 96.2 g of DL-α-tocopherol and 0.38 g of potassium hydroxide, as the base catalyst, were loaded. After the inside of the vessel was replaced with nitrogen gas, the temperature was increased to 100-110° C., and the dehydration was conducted for 0.5 hours. Then, the temperature was increased to 130-140° C., 25.9 g of 1,2-butylene oxide was injected over the course of 0.5 hours, and then aging was carried out for 3.0 hours. Subsequently, 137.5 g of ethylene oxide was injected over the course of 1.5 hours, and then aging was carried out for 2.0 hours.

After the completion of aging, the cooling was carried out. Into a beaker, 240.0 g of the synthesized DL-α-tocopherol ethylene oxide/butylene oxide/ethylene oxide (k=14, m=2, n=0) was taken and loaded, the temperature was increased to 100-110° C., and the dehydration was conducted. After dehydration, the cooling was carried out, and then 10.21 g of phosphoric anhydride was added in installments while the temperature was being increased from 40° C. to 80° C. The aging was carried out at 80° C. for 4.5 hours, and then the cooling was carried out, and 70 g of methanol and 9.71 g of potassium methylate (=potassium methoxide) were added. After filtering the obtained methanol solution, the methanol was removed, and 171.3 g (yield: 68.5%) of the desired product was obtained.

Production Example 15

Disodium salt of DL-α-tocopherol ethylene oxide/butylene oxide/ethylene oxide addition product sulfosuccinic acid [in the above-described formula (I), k=14, m=2, n=2, $R_1$, $R_2$, $R_3$=$CH_3$, $R_4$=disodium salt of $COCH_2CH(SO_3H)COOH$]

Into an autoclave, 100.0 g of the DL-α-tocopherol ethylene oxide/butylene oxide/ethylene oxide addition product (k=14, m=2, n=2), which was synthesized in Production Example 12, was taken and placed, and 7.84 g of maleic anhydride and 0.50 g of anhydrous sodium acetate were loaded. After the inside of the vessel was replaced with nitrogen gas, the temperature was increased to 70-80° C., and the esterification reaction was carried out for 3 hours. The thus obtained reaction product, namely, 106.1 g of maleate of DL-α-tocopherol ethylene oxide/butylene oxide/ethylene oxide addition product was loaded into a four-neck flask containing 10.1 g of anhydrous sodium sulfite beforehand dissolved in 174.3 g of pure water at 40-50° C. The temperature was increased to 70-80° C. to carry out sulfonation, and stirring was carried out at the same temperature for 3.0 hours. The reaction solution was cooled, the pH was adjusted to 6.5 with 20% sodium hydroxide aqueous solution, and 290.0 g (yield: 98.0%) of the aqueous solution of the desired product was obtained.

Production Example 16

Sodium salt of DL-α-tocopherol ethylene oxide/butylene oxide/ethylene oxide addition product acetic acid [in the above-described formula (I), k=14, m=2, n=2, $R_1$, $R_2$, $R_3$=$CH_3$, $R_4$=$CH_3COONa$]

Into a four-neck flask, 25.0 g of the DL-α-tocopherol ethylene oxide/butylene oxide/ethylene oxide addition product (k=14 μm=2, n=2), which was synthesized in Production Example 12, was taken and loaded, and 750 mL of toluene was added. Under a nitrogen atmosphere, azeotropic dehydration was carried out at 100-110° C. for 1 hour, and then cooling to 30° C. was carried out. After the addition of 32.0 mL of 1.0 M-potassium tert-butoxide/tert-butanol solution, stirring was carried out at room temperature for 1 hour. After 1 hour, 18.68 g of ethyl bromoacetate was added, and the reaction was carried out under reflux for 2 hours while being stirred at 110° C. After the reaction, cooling to 30° C. was carried out, and stirring was carried out at room temperature for 18 hours. After the completion of stirring, filtration was carried out with the use of Celite. Toluene was removed with an evaporator, and 20.5 g of the carboxylic acid ethyl ester of DL-α-tocopherol ethylene oxide/butylene oxide/ethylene oxide addition product was obtained. Subsequently, 20.5 g of the carboxylic acid ethyl ester and 200 mL of 1 N—NaOH were loaded into a four-neck flask, and the reaction was carried out at room temperature for 4 hours. After the completion of the reaction, the solution was cooled to 5° C., and the pH was adjusted to 3 with 2 N—HCl. The reaction solution was extracted with 100 mL of methylene chloride five times. After washing with 50 mL of pure water, the solvent was removed, and 20.1 g of the carboxylic acid was obtained. The carboxylic acid (20.1 g) was dissolved in 100 mL of methanol, and a methanol solution containing 0.83 g of sodium methoxide was added. After sodium replacement, the solvent was removed, and 20.2 g (yield: 75.9%) of the desired product was obtained.

Comparative Example 1

DL-α-Tocopherol ethylene oxide addition product [vitamin E derivative represented by the following formula (III)]

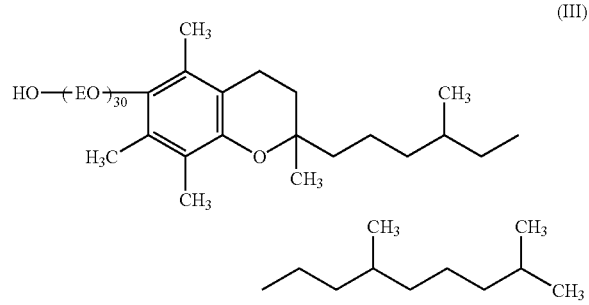

(III)

Into an autoclave, 50.7 g of DL-α-tocopherol and 0.20 g of potassium hydroxide, as the base catalyst, were loaded. After the inside of the vessel was replaced with nitrogen gas, the temperature was increased to 100-110° C., and the dehydration was conducted for 0.5 hours. Then, the temperature was increased to 130-140° C., 155.3 g of ethylene oxide was injected over the course of 4.0 hours. While the same temperature was being maintained, aging was carried out for 2.0 hours. After the completion of aging, the cooling was carried out, and the product was neutralized with phosphoric acid aqueous solution and purified. The formed salt was filtered, and 172.0 g (yield: 83.4%) of the desired compound represented by the above-described formula (III), was obtained.

Infrared absorption spectrum ν $cm^{-1}$ (neat): 2865.9, 1458.7, 1350.7, 1252.2, 1104.9, 946.3.

Comparative Example 2

DL-α-Tocopherol propylene oxide/ethylene oxide addition product [vitamin E derivative represented by the following formula (IV), in the formula, "EO" represents an ethylene oxide group and "PO" represents a propylene oxide group.]

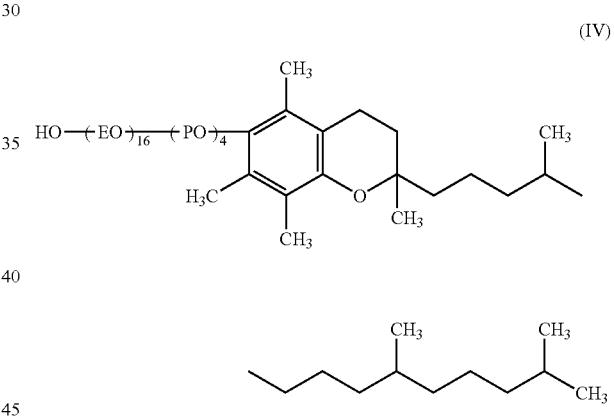

(IV)

Into an autoclave, 94.5 g of DL-α-tocopherol and 0.38 g of potassium hydroxide, as the base catalyst, were loaded. After the inside of the vessel was replaced with nitrogen gas, the temperature was increased to 100-110° C., and the dehydration was conducted for 0.5 hours. Then, the temperature was increased to 130-140° C., and 50.9 g of propylene oxide was injected over the course of 1.5 hours. While the same temperature was being maintained, aging was carried out for 2.0 hours. Subsequently, 154.5 g of ethylene oxide was injected over the course of 1.5 hours, and then aging was carried out for 2.0 hours. After the completion of aging, the cooling was carried out, and the product was neutralized with phosphoric acid aqueous solution and purified. The formed salt was filtered, and 246.5 g (yield: 82.1%) of the desired product, which is represented by the above-described formula (IV), was obtained.

Infrared absorption spectrum ν $cm^{-1}$ (neat): 2866.6, 1458.2, 1375.8, 1254.9, 1108.9, 938.5.

Comparative Example 3

Sodium salt of DL-α-tocopherol ethylene oxide/propylene oxide/ethylene oxide addition product sulfuric acid ester [vitamin E derivative salt represented by the following formula (V), in the formula, "EO" represents an ethylene oxide group and "PO" represents a propylene oxide group.]

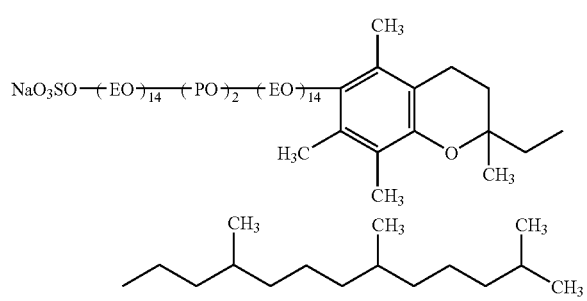

(V)

Into an autoclave, 60.5 g of DL-α-tocopherol (manufactured by Wako Pure Chemical Industries, Ltd.) and 0.24 g of potassium hydroxide, as the alkaline catalyst, were loaded. After the inside of the vessel was replaced with nitrogen gas, the temperature was increased to 100-110° C., and the dehydration was conducted for 0.5 hours. Then, the temperature was increased to 130-140° C., and 86.5 g of ethylene oxide (Nippon Shokubai Co., Ltd.) was injected over the course of 1.5hours. While the same temperature was being maintained, aging was carried out for 1.0 hour. Subsequently, 16.3 g of propylene oxide (Nippon Shokubai Co., Ltd.) was injected over the course of 0.5 hours, and then aging was carried out for 2.0 hours. Lastly, 86.3 g of ethylene oxide was injected over the course of 1.0 hour, and then aging was carried out for 1.0 hour. After the completion of aging, the cooling was carried out, and the product was neutralized with phosphoric acid aqueous solution and purified. The formed salt was filtered, and the DL-α-tocopherol ethylene oxide/propylene oxide/ethylene oxide addition product (compound in which the terminal group, namely $NaO_3SO$ group, of the compound represented by the above-described formula (V) is replaced with an OH group) was obtained. Subsequently, 50.4 g of the above-described synthesized vitamin E derivative was placed into a four-neck flask, the temperature was increased to 100-110° C., and the dehydration was conducted. While the same temperature was being maintained, 0.81 g of urea and 3.96 g of sulfamic acid were added in installments. The aging was carried out at the same temperature for 3 hours, and then the cooling was carried out. After 50 g of methanol and 1.3 g of aqueous ammonia were added, filtration was conducted. To the obtained solution, 2.5 g of 50% sodium hydroxide aqueous solution was added, the methanol was removed by heating, and 49.0 g (yield: 91.8%) of the desired product, which is represented by the above-described formula (V), was obtained.

Infrared absorption spectrum ν cm$^{-1}$ (neat): 2868.2, 1459.6, 1348.8, 1253.6, 1105.7, 1032.3, 859.7, 946.8.

Comparative Example 4

Potassium salt of DL-α-tocopherol ethylene oxide/propylene oxide/ethylene oxide addition product sulfuric acid ester [vitamin E derivative salt represented by the following formula (VI), in the formula, "EO" represents an ethylene oxide group and "PO" represents a propylene oxide group.]

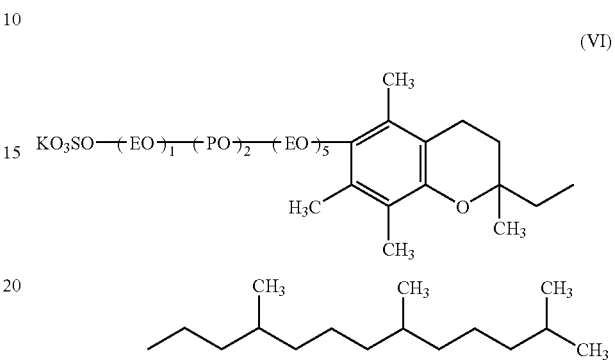

(VI)

Into an autoclave, 212.2 g of DL-α-tocopherol and 0.64 g of potassium hydroxide, as the alkaline catalyst, were loaded. After the inside of the vessel was replaced with nitrogen gas, the temperature was increased to 100-110° C., and the dehydration was conducted for 0.5 hours. Then, the temperature was increased to 130-140° C., and 21.7 g of ethylene oxide was injected over the course of 0.5 hours. While the same temperature was being maintained, aging was carried out for 2.0 hours. Subsequently, 57.1 g of propylene oxide was injected at 130-140° C. over the course of 0.5 hours, and then aging was carried out for 3.0 hours. Lastly, 108.4 g of ethylene oxide was injected at 130-140° C. over the course of 1.5 hours, and then aging was carried out for 2.0 hours. After the completion of aging, the cooling was carried out. Into a four-neck flask, 343.1 g of the synthesized DL-α-tocopherol ethylene oxide/propylene oxide/ethylene oxide addition product (compound in which the terminal group, namely $KO_3SO$ group, of the compound represented by the above-described formula (VI) is replaced with an OH group) was taken and loaded, and the temperature was increased to 100-110° C. To this was added 0.21 g of monosodium phosphate, and 2.09 g of urea and 41.7 g of sulfamic acid were added while the same temperature was being maintained. At the same temperature, aging was carried out for 6 hours while the sulfamic acid was being added. Then the cooling was carried out, 400 g of methanol and 6.0 g of aqueous ammonia were added, and the filtration was conducted. To the obtained filtrate, 21.0 g of potassium hydroxide was added, the methanol was removed by heating, 240 g of ethanol was subsequently added, and the filtration was conducted. The filtrate was heated, the excess ethanol was removed, and 385 g (yield: 85%) of the desired product, which is represented by the above-described formula (VI), was obtained.

Structural analysis results based on multiple-collision induced dissociation (MS$^3$) mass spectrum (electrospray (negative ion detection), helium collision gas)

The product was confirmed, from the following data, to be the potassium salt of DL-α-tocopherol ethylene oxide/propylene oxide/ethylene oxide addition product sulfuric acid ester represented by the above-described structural formula.

Mass spectrum (electrospray (negative ion detection))

(1) m/z 889.57: ion obtained by potassium removal, $C_{47}H_{85}O_{13}S_1$

MS/MS (2) m/z 459: (1)—430 (tocopherol)

(3) m/z 415: (2)—44 (EO)

MS/MS/MS (4) m/z 357: (3)—58 (PO)

MS/MS/MS/MS (5) m/z 299: (4)—58 (PO)

MS/MS/MS/MS/MS (6) m/z 255: (5)—44 (EO)

(7) m/z 211: (5)—88 (2EO)

Test Example 1

Test of Moisture Retaining Property

On a filter paper that is 2 cm by 2 cm square, 10 µL of each sample was dropped. The samples were from the above-described Production Examples 1, 3, and 6, and from Comparative Examples 1, 2, and 3, and water. The mass change was measured every 5 minutes at 25° C. under a humidity of 50%. The value n in the formula, (nX+m), which is derived by the least-squares method of the results is set to be the water evaporation rate constant. The average values of total three data for each sample, plotted as absolute values, were determined. The smaller the water evaporation rate constant, the higher the moisture retaining effect. The results are shown in FIG. 1.

As is clear from FIG. 1, the moisture retaining properties of the vitamin E derivatives (salt) of Production Examples 1, 3, and 6 were confirmed to be better compared with those of the vitamin E derivatives (salt) of Comparative Examples 1, 2, and 3.

Test Example 2

Test of Solubilizing Ability

As shown in Table 1, samples were prepared by blending 0.05 mass % or 0.1 mass % of a material to be solubilized, 3 mass % of a solubilizing agent, 5 mass % of ethanol, and the balance of ion-exchanged water.

As the material to be solubilized, five kinds of oil components, namely, vitamin E acetate, trioctanoin, isohexadecane, decamethylcyclopentasiloxane, and perfume were used.

As the solubilizing agent, Production Examples 1, 2, and 6, Comparative Examples 1, 2, 3, and 4, and POE (60 mol) hydrogenated castor oil, which is a nonionic surfactant and widely used as a solubilizing agent and emulsifier, were used.

TABLE 1

| Components | Content (Mass %) |
|---|---|
| Ion-exchanged water | to 100 |
| Ethanol | 5 |
| Material to be solubilized (vitamin E acetate, decamethylcyclopentasiloxane, isohexadecane, trioctanoin, perfume) | 0.05, 0.1 |
| Solubilizing agent (Production Examples 1, 2 and 6, Comparative- Examples 1, 2, 3 and 4, POE (60 mol) hydrogenated castor oil) | 3 |

The solubilizing ability was investigated with use of the above-described respective samples. The solubilizing ability was determined by measuring the turbidity at 25° C. with an integration type turbidimeter TR-35 (manufactured by the former Mitsubishi Chemical Corporation, which is presently Dia Instruments Co. Ltd.) and a glass cell (width: 50 mm, depth: 30 mm, height: 50 mm; manufactured by Mitsubishi Chemical Corporation). The results are shown in Tables 2 and 3.

TABLE 2

|  |  | Turbidity by blending 0.05 mass % of a material to be solubilized | | | | |
|---|---|---|---|---|---|---|
|  |  | Vitamin E acetate | Trioctanoin | Isohexadecane | Decamethyl-cyclopentasiloxane | Perfume |
| Solubilizing agent | Production Example 1 | 1.3 | 20.9 | 19.2 | 21.4 | 1.6 |
|  | Production Example 2 | 1.9 | 19.5 | 15.8 | 18.8 | 2.4 |
|  | Production Example 6 | 1.1 | 15.6 | 23.4 | 24.0 | 1.1 |
|  | Comparative Example 1 | 2.0 | 6.4 | 46.2 | 53.2 | 5.8 |
|  | Comparative Example 2 | 10.2 | 5.7 | 22.6 | 38.5 | 15.1 |
|  | Comparative Example 3 | 4.0 | 19.3 | 24.8 | 25.1 | 2.9 |
|  | Comparative Example 4 | 4.0 | 21.5 | 17.0 | 35.7 | 3.0 |
|  | POE (60 mol) hydrogenated castor oil | 7.1 | 11.7 | 64.9 | 83.4 | 2.1 |

TABLE 3

| | | Turbidity by blending 0.1 mass % of a material to be solubilized | | | | |
|---|---|---|---|---|---|---|
| | | Vitamin E acetate | Trioctanoin | Isohexadecane | Decamethyl-cyclopentasiloxane | Perfume |
| Solubilizing agent | Production Example 1 | 1.7 | 2.9 | 4.2 | 17.8 | 5.2 |
| | Production Example 2 | 1.8 | 13.7 | 15.1 | 15.5 | 5.2 |
| | Production Example 6 | 1.7 | 5.0 | 13.7 | 15.6 | 4.0 |
| | Comparative Example 1 | 5.3 | 41.9 | 78.9 | 76.1 | 6.7 |
| | Comparative Example 2 | 10.6 | 15.1 | 67.8 | 76.2 | 5.4 |
| | Comparative Example 3 | 16.9 | 33.6 | 65.4 | 41.2 | 6.9 |
| | Comparative Example 4 | 3.0 | 31.5 | 47.0 | 45.7 | 4.5 |
| | POE (60 mol) hydrogenated castor oil | 10.3 | 43.2 | 56.3 | 56.4 | 18.6 |

As is clear from the results shown in Tables 2 and 3, the turbidity was 20 or lower for all Production Examples 1, 2, and 6; thus it was confirmed that their solubilizing ability was excellent. On the other hand, the turbidity exceeded 20 for some of Comparative Examples 1 to 4 and POE (60 mol) hydrogenated castor oil; thus it was confirmed that their solubilizing ability was inferior.

Test Example 3
Test for Emulsifying Ability

The oil phase containing 2 mass % of squalane, trioctanoin, or dimethyl silicone (6 mPa·s), as the material to be emulsified, and 1 mass % of Production Example 1, Comparative Example 1, Comparative Example 2, Comparative Example 3, or POE (60 mol) hydrogenated castor oil, as an emulsifier, was gradually added, for emulsification, to the water phase containing ion-exchanged water (balance) and ethanol (3 mass %) and being stirred with a homomixer at 9000 rpm; thus Samples 1 to 15 shown in Table 4 were prepared. The emulsion particles were visually observed with an optical microscope, and the emulsion particle size (μm) was measured. The results are shown in Table 4. In the table, the value in the parenthesis of the emulsion particle size indicates the size of dotted emulsion particles observed in the emulsion.

TABLE 4

| | | Test for emusifying ability | | | | | | | | |
|---|---|---|---|---|---|---|---|---|---|---|
| | | Sample 1 | Sample 2 | Sample 3 | Sample 4 | Sample 5 | Sample 6 | Sample 7 | Sample 8 | Sample 9 |
| Water | Ion-exchanged water | Balance | Balance | Balance | Balance | Balance | Balance | Balance | Balance | Balance |
| Alcohol | Ethanol | 3 | 3 | 3 | 3 | 3 | 3 | 3 | 3 | 3 |
| Emulsifier | Vitamin E derivative of Production Example 1 | 1 | 1 | 1 | — | — | — | — | — | — |
| | Vitamin E derivative of Comparative Example 1 | — | — | — | 1 | 1 | 1 | — | — | — |
| | Vitamin E derivative of Comparative Example 2 | — | — | — | — | — | — | 1 | 1 | 1 |
| | Vitamin E derivative of Comparative Example 3 | — | — | — | — | — | — | — | — | — |
| | POE (60 mol) hydrogenated castor oil | — | — | — | — | — | — | — | — | — |
| Oil | Squalane | 2 | — | — | 2 | — | — | 2 | — | — |
| | Trioctanoin | — | 2 | — | — | 2 | — | — | 2 | — |
| | Dimethylsilicone (6 mPa·s) | — | — | 2 | — | — | 2 | — | — | 2 |
| | | ~5(10) | ~5(10) | ~5(10) | ~5(10) | ~15 | ~20 | ~40 | ~50 | ~40 |

| | | Test for emusifying ability | | | | | |
|---|---|---|---|---|---|---|---|
| | | Sample 10 | Sample 11 | Sample 12 | Sample 13 | Sample 14 | Sample 15 |
| Water | Ion-exchanged water | Balance | Balance | Balance | Balance | Balance | Balance |
| Alcohol | Ethanol | 3 | 3 | 3 | 3 | 3 | 3 |
| Emulsifier | Vitamin E derivative of Production Example 1 | — | — | — | — | — | — |
| | Vitamin E derivative of Comparative Example 1 | — | — | — | — | — | — |
| | Vitamin E derivative of Comparative Example 2 | — | — | — | — | — | — |
| | Vitamin E derivative of Comparative Example 3 | 1 | 1 | 1 | — | — | — |
| | POE (60 mol) hydrogenated castor oil | — | — | — | 1 | 1 | 1 |
| Oil | Squalane | 2 | — | — | 2 | — | — |
| | Trioctanoin | — | 2 | — | — | 2 | — |
| | Dimethylsilicone (6 mPa·s) | — | — | 2 | — | — | 2 |
| | | ~50 | ~40 | ~40 | ~50 | ~10 | ~10 |

As is clear from the results in Table 4, the emulsion particle sizes of Samples 1 to 3, in which Production Example 1 was used, were very small.

Test Example 4

Sensory Evaluation for Feeling in Use

The sensory evaluation for the feeling in use was conducted with the use of Samples 16 to 23 (lotion) having compositions shown in Table 5. The evaluation of the feeling in use was conducted for the (1) affinity for the skin, (2) stickiness and moist feeling, and (3) permeation feeling, with the actual usage test by 10 professional female panelists according to the following method. The evaluation was based on the respective evaluation criteria.

[Feeling in Use (Affinity for the Skin)]

The actual usage test by 10 professional female panelists was conducted for the spreadability on the skin. The evaluation was based on the following evaluation criteria.

(Evaluation Criteria)
⊚: All 10 panelists evaluated that the affinity for the skin was good during use.
○: 7 to 9 panelists evaluated that the affinity for the skin was good during use.
Δ: 3 to 6 panelists evaluated that the affinity for the skin was good during use.
x: 0 to 2 panelists evaluated that the affinity for the skin was good during use.

[Feeling in Use (Sticky Feeling)]

The actual usage test by 10 professional female panelists was conducted for the sticky feeling during drying after the application on the skin. The evaluation was based on the following evaluation criteria.

(Evaluation Criteria)
⊚: All 10 panelists evaluated that there was no stickiness during drying and there was a moist feeling in use.
○: 7 to 9 panelists evaluated that there was no stickiness during drying and there was a moist feeling in use.
Δ: 3 to 6 panelists evaluated that there was no stickiness during drying and there was a moist feeling in use.
x: 0 to 2 panelists evaluated that there was no stickiness during drying and there was a moist feeling in use.

[Feeling in Use (Light Fresh Feeling)]

The actual usage test by 10 professional female panelists was conducted for the light fresh feeling. The evaluation was based on the following evaluation criteria.

(Evaluation Criteria)
⊚: All 10 panelists evaluated that there was a light fresh feeling in use.
○: 7 to 9 panelists evaluated that there was a light fresh feeling in use.
Δ: 3 to 6 panelists evaluated that there was a light fresh feeling in use.
x: 0 to 2 panelists evaluated that there was a light fresh feeling in use.

[Feeling in Use (Permeation Feeling)]

The actual usage test by 10 professional female panelists was conducted for the permeation feeling. The evaluation was based on the following evaluation criteria.

(Evaluation Criteria)
⊚: All 10 panelists evaluated that there was a permeation feeling in use.
○: 7 to 9 panelists evaluated that there was a permeation feeling in use.
Δ: 3 to 6 panelists evaluated that there was a permeation feeling in use.
X: 0 to 2 panelists evaluated that there was a permeation feeling in use.

The results are shown in Table 5.

TABLE 5

| | Component (mass %) | | | | | | | |
|---|---|---|---|---|---|---|---|---|
| | Sample 16 | Sample 17 | Sample 18 | Sample 19 | Sample 20 | Sample 21 | Sample 22 | Sample 23 |
| Ion-exchanged water | Balance | Balance | Balance | Balance | Balance | Balance | Balance | Balance |
| Ethenol | 5 | 5 | 5 | 5 | 5 | 5 | 5 | 5 |
| Perfume (material to be solubilized) | 0.05 | 0.05 | 0.05 | 0.05 | 0.05 | 0.05 | 0.05 | 0.05 |
| Production Example 1 (emulsifier) | 1 | — | — | — | — | — | — | — |
| Production Example 2 (emulsifier) | — | 1 | — | — | — | — | — | — |
| Production Example 3 (emulsifier) | — | — | 1 | — | — | — | — | — |
| Comparative Example 1 (emulsifier) | — | — | — | 1 | — | — | — | — |
| Comparative Example 2 (emulsifier) | — | — | — | — | 1 | — | — | — |
| Comparative Example 3 (emulsifier) | — | — | — | — | — | 1 | — | — |
| Comparative Example 4 (emulsifier) | — | — | — | — | — | — | 1 | — |
| POE (60 mol) hydrogenated castor oil (emulsifier) | — | — | — | — | — | — | — | 1 |
| Affinity for the skin | ⊚ | ○ | ○ | ⊚ | ○ | Δ | ⊚ | X |
| Sticky feeling | ⊚ | ⊚ | ⊚ | ○ | Δ | Δ | Δ | X |
| Light fresh feeling | ⊚ | ⊚ | ⊚ | Δ | Δ | ○ | ⊚ | X |
| Permeation feeling | ⊚ | ⊚ | ○ | ○ | Δ | ○ | ⊚ | X |

More formulation examples are shown below.

Example 1

O/W Type Milky Lotion

| (Component) | (Mass %) |
|---|---|
| (1) Ion exchanged water | Balance |
| (2) Dipropylene glycol | 5.0 |
| (3) 1,3-butylene glycol | 1.0 |
| (4) Vaseline | 1.0 |
| (5) Pentaerythrityl tetraoctanoate | 3.0 |
| (6) Trimethylsiloxy silicate (50% solution)(*1) | 1.0 |
| (7) Cetyl alcohol | 0.5 |
| (8) Stearyl alcohol | 0.5 |
| (9) PEG-60 glyceryl isostearate | 0.3 |
| (10) Vitamin E derivative of Production Example 1 | 0.5 |
| (11) PEG-5 glyceryl stearate | 0.5 |
| (12) Dipotassium glycyrrhizinate | 0.1 |
| (13) Vitamin E acetate | 0.5 |
| (14) Gambir extract | 0.1 |
| (15) Beech bud extract | 0.1 |
| (16) Turmeric extract | 0.1 |
| (17) Phenoxyethanol | 0.2 |
| (18) Perfume | 0.1 |

(*1)BY11-018 (50% decamethylcyclopentasiloxane solution; manufactured by Toray Dow Corning Silicone Co., Ltd.)

<Preparation>

Into component (1), components (2), (3), (12), and (14) to (17) were added and dissolved, and a water phase at 70° C. was prepared by heating. Separately, an oil phase was prepared by heating a mixture of (4), (5) to (11), (13), and (18) to 70° C. This oil phase was added to the water phase, and the emulsification was carried out with a homomixer. The emulsion particle size was 5 μm or smaller. After the completion of emulsification, the desired O/W type milky lotion was obtained by rapidly cooling to 40° C. or lower and by carrying out dehydration and filtration.

<Product Properties>

For the obtained O/W type milky lotion, similar evaluations to Test Examples 3 and 4 were conducted. As a result, it was found that the vitamin E derivative of Production Example 1 had an excellent emulsifying ability and the feeling in use was excellent (evaluation of feeling in use: the affinity for the skin, sticky feeling, light fresh feeling, and permeation feeling were all ⊚).

Example 2

Gel Essence

| (Component) | (Mass %) |
|---|---|
| (1) Ion exchanged water | Balance |
| (2) Alkyl-modified carboxyvinyl polymer | 0.1 |
| (3) Carboxyvinyl polymer | 0.4 |
| (4) Ethanol | 3.0 |
| (5) 1,3-butylene glycol | 4.0 |
| (6) Glycerin | 1.0 |
| (7) PEG-20 | 1.0 |
| (8) Polyvinyl alcohol | 0.1 |
| (9) Cetyl octanoate | 3.0 |
| (10) Dimetylpolysiloxane (6 mPa·s) | 3.0 |
| (11) Vitamin E derivative of Production Example 2 | 1.0 |
| (12) Behenyl alcohol | 0.1 |
| (13) Potassium hydroxide | 0.1 |
| (14) Safflower extract | 0.1 |
| (15) Poria cocos extract | 0.1 |
| (16) White lily extract | 0.1 |
| (17) Phenoxyethanol | 0.1 |
| (18) Perfume | 0.1 |
| (19) Coloring material | 0.1 |

<Preparation>

Into component (1) in the main pot, components (2), (3), (6), (7), (13) to (17), and (19) were added and dissolved. In separate pots, component (11) was dissolved in component (4), and component (8) was dissolved in component (5) by heating. A water phase was prepared by adding these solutions to the main pot. Separately, an oil phase was prepared by uniformly dissolving components (9), (10), (12), and (18) at 70° C. While the water phase at 70° C. was being treated with a homomixer, the oil phase at 70° C. was gradually added to emulsify it. The emulsion particle size was 10 to 30 μm. After the completion of emulsification, the desired gel essence was obtained by rapidly cooling to 40° C. or lower and by carrying out dehydration and filtration.

<Product Properties>

For the obtained gel essence, similar evaluations to Test Examples 3 and 4 were conducted. As a result, it was found that the vitamin E derivative of Production Example 2 had an excellent emulsifying ability and the feeling in use was excellent (evaluation of feeling in use: the affinity for the skin, sticky feeling, light fresh feeling, and permeation feeling were all ⊚).

Example 3

Lotion

| (Component) | (Mass %) |
|---|---|
| (1) Ion exchanged water | Balance |
| (2) Ethanol | 5.0 |
| (3) Glycerin | 2.0 |
| (4) Dipropylene glycol | 5.0 |
| (5) Xylitol | 1.0 |
| (6) Polyethylene glycol 1000 | 0.5 |
| (7) Vitamin E derivative of Production Example 4 | 0.5 |
| (8) Salicylic acid | 0.1 |
| (9) Dipotassium glycyrrhizinate | 0.05 |
| (10) *Houttuynia* herb extract | 0.6 |
| (11) Saxifrage sarmentosa extract | 0.1 |
| (12) Sodium citrate | 0.35 |
| (13) Sodium hexametaphosphate | 0.01 |
| (14) Phenoxyethanol | 0.3 |
| (15) Perfume | 0.001 |
| (16) Dimethylsilicone (6 mPa·s) | 0.02 |

<Preparation>

To a mixture of components (2) and (7), components (14) to (16) were added (alcohol part). On the other hand, components (3) to (6) and (8) to (13) were added in series to component (1) and uniformly dissolved. To this was added the alcohol part, and the desired lotion was obtained by dissolving uniformly with stirring.

<Product properties>

For the obtained lotion, similar evaluations to Test Examples 2 and 4 were conducted. As a result, it was found that the turbidity was 12.0, the solubilization of dimethyl silicone and perfumes were excellent, and the feeling in use was excellent (evaluation of feeling in use: the affinity for the skin, sticky feeling, light fresh feeling, and permeation feeling were all ⊚).

Example 4

Whitening Lotion

| (Component) | (Mass %) |
|---|---|
| (1) Ion exchanged water | Balance |
| (2) Ethanol | 3.0 |
| (3) Glycerin | 5.0 |
| (4) 1,3-butylene glycol | 4.0 |
| (5) POE (3 mol) methyl glucoside | 2.0 |
| (6) POE (14 mol) POP (7 mol) dimethyl eter | 1.0 |
| (7) Xanthan gum | 0.1 |
| (8) Vitamin E derivative of Production Example 5 | 0.3 |
| (9) Potassium 4-methoxy-salicylate | 1.0 |
| (10) Dipotassium glycyrrhizinate | 0.05 |
| (11) L-serine | 0.001 |
| (12) Ethyl ascorbic acid | 0.1 |
| (13) Calcium chloride | 0.001 |
| (14) Magnesium chloride | 0.002 |
| (15) Shinleaf extract | 0.01 |
| (16) Ononis extract | 0.1 |
| (17) Saiko extract | 0.05 |
| (18) Tocopherol | 0.001 |
| (19) Citric acid (food grade) | 0.02 |
| (20) Sodium citrate | 0.08 |
| (21) Phenoxyethanol | 0.5 |
| (22) Perfume | 0.1 |
| (23) Tripropylene glycol dineopentanoate | 0.05 |

<Preparation>
To a mixture of components (2) and (8), components (18) and (21) to (23) were added (alcohol part). On the other hand, components (3) to (7), (9) to (17), and (19) to (20) were added in series to component (1) and dissolved. To this was added the alcohol part, and the desired whitening lotion was obtained by dissolving uniformly with stirring.

<Product Properties>
For the obtained lotion, similar evaluations to Test Examples 2 and 4 were conducted. As a result, it was found that the turbidity was 19.0, the solubilization of tripropylene glycol dineopentanoate and perfume was excellent, and the feeling in use was excellent (evaluation of feeling in use: the affinity for the skin, sticky feeling, light fresh feeling, and permeation feeling were all ⊚).

Example 5

Whitening Lotion

| (Component) | (Mass %) |
|---|---|
| (1) Ion exchanged water | Balance |
| (2) Ethanol | 8.0 |
| (3) Glycerin | 2.5 |
| (4) Dipropylene glycol | 3.0 |
| (5) Polyethylene glycol 1500 | 3.0 |
| (6) Vitamin E derivative of Production Example 7 | 0.4 |
| (7) Tranexamic acid | 2.0 |
| (8) Maltitol | 0.1 |
| (9) L-lysine hydrochloride | 0.001 |
| (10) Sophora angustifolia extract | 0.001 |
| (11) Rose extract | 0.001 |
| (12) Marine collagen solution | 0.01 |
| (13) Betaine lauryl sulfate | 0.015 |
| (14) Isostearic acid | 0.01 |
| (15) Citric acid | 0.002 |
| (16) Sodium citrate | 0.008 |
| (17) Sodium pyrosulfite | 0.003 |
| (18) Sodium edetate | 0.03 |
| (19) Phenoxyethanol | 0.35 |
| (20) Perfume | 0.03 |
| (21) Isotridecyl isononanoate | 0.02 |

<Preparation>
To a mixture of components (2) and (6), components (14) and (19) to (21) were added (alcohol part). On the other hand, components (3) to (5), (7) to (13), and (15) to (18) were added in series to component (1) and dissolved. To this was added the alcohol part, and the desired whitening lotion was obtained by dissolving uniformly with stirring.

<Product Properties>
For the obtained lotion, similar evaluations to Test Examples 2 and 4 were conducted. As a result, it was found that the turbidity was 15.9, the solubilization of isotridecyl isononanoate and perfume was excellent, and the feeling in use was excellent (evaluation of feeling in use: the affinity for the skin, sticky feeling, light fresh feeling, and permeation feeling were all ⊚).

Example 6

Whitening Lotion

| (Component) | (Mass %) |
|---|---|
| (1) Ion-exchanged water | Balance |
| (2) Ethanol | 5.0 |
| (3) Glycerin | 8.5 |
| (4) Dipropylene glycol | 5.0 |
| (5) Xanthan gum | 0.06 |
| (6) Vitamin E derivative of Production Example 9 | 1.0 |
| (7) Ascorbic acid glucoside | 2.0 |
| (8) Dipotassium glycyrrhizinate | 0.05 |
| (9) Hydrogenated phospholipid | 0.01 |
| (11) 2-phosphorylcholine/butylmethacrylate copolymer solution | 0.01 |
| (12) Hyaluronic acid | 0.001 |
| (13) Paeonia suffruticosa root extract | 0.05 |
| (14) Potassium hydroxide | 0.4 |
| (15) Citric acid | 0.03 |
| (16) Sodium citrate | 0.17 |
| (17) Sodium edetate | 0.1 |
| (18) Paraben | 0.2 |
| (19) Perfume | 0.3 |
| (20) Decamethylcyclopentasiloxane | 0.1 |

<Preparation>
To a mixture of components (2) and (6), components (18) to (20) were added (alcohol part). On the other hand, components (3) to (5) and (8) to (17) were added in series to component (1) and dissolved. To this was added the alcohol part, and the desired whitening lotion was obtained by dissolving uniformly with stirring.

<Product Properties>
For the obtained lotion, similar evaluations to Test Examples 2 and 4 were conducted. As a result, it was found that the turbidity was 11.5, the solubilization of decamethylcyclopentasiloxane and perfume was excellent, and the feeling in use was excellent (evaluation of feeling in use: the affinity for the skin, sticky feeling, light fresh feeling, and permeation feeling were all ⊚).

Example 7

Whitening Cream

| (Component) | (Mass %) |
|---|---|
| (1) Liquid paraffin | 2.0 |
| (2) Decamethylcyclopentasiloxane | 6.0 |
| (3) Isodecyl benzoate | 6.0 |
| (4) Vitamin E derivative of Production Example 10 | 3.0 |
| (5) Cetearyl glucoside ("MONTANOV 68" manufactured by SEPIC Co., Ltd.) | 0.5 |
| (6) Cetyl alcohol | 2.5 |
| (7) Batyl alcohol | 2.5 |
| (8) Perfume | 0.1 |
| (9) Ion-exchanged water | Balance |
| (10) 1,3-butylene glycol | 3.0 |
| (11) Ascorbic acid glucoside | 2.0 |
| (12) Paraben | 0.15 |
| (13) Ethanol | 3.0 |
| (14) Sodium hydroxide | 0.4 |
| (15) Vinylpyrrolidone/2-acrylamide-2-methylpropanesulfonic acid copolymer ("ASRISTOFLEX AVC" manufactured by CLARIANT Corp.) | 0.5 |
| (16) Citric acid | 0.09 |
| (17) Sodium citrate | 0.01 |

<Preparation>

Components (1) to (8) were mixed and uniformly dissolved at 70° C. (oil phase). On the other hand, components (9) to (17) were mixed and uniformly dissolved at 70° C. (water phase). The emulsification was carried out with a homomixer while gradually adding the oil phase to the water phase maintained at 70° C. The emulsion particle size was 5 to 10 μm. After the completion of emulsification, the desired skin cream was obtained by rapidly cooling to 40° C. or lower.

<Product Properties>

For the obtained skin cream, similar evaluations to Test Examples 13 and 4 were conducted. As a result, it was found that the vitamin E derivative of Production Example 10 had an excellent emulsifying ability and the feeling in use was excellent (evaluation of feeling in use: the affinity for the skin, sticky feeling, light fresh feeling, and permeation feeling were all ⊚).

Example 8

Hair Styling Cream

| (Component) | (Mass %) |
|---|---|
| (1) Isoparaffin | 3.0 |
| (2) Dimethylpolysiloxane (20 mPa·s) | 7.0 |
| (3) Propylene glycol dicaprylate | 5.0 |
| (4) Stearyl alcohol | 2.0 |
| (5) Batyl alcohol | 2.0 |
| (6) POE (6 mol) oleyl ether | 0.3 |
| (7) Vitamin E derivative of Production Example 11 | 4.0 |
| (8) Perfume | 0.1 |
| (9) Hydrolyzed silk | 0.1 |
| (10) Ion-exchanged water | Balance |
| (11) Glycerin | 2.5 |
| (12) Ethanol | 3.0 |
| (13) Phenoxyethanol | 0.5 |
| (14) Carboxyvinyl polymer | 0.2 |
| (15) Potassium hydroxide | 0.05 |
| (16) Sodium acrylate/2-acrylamide-2-methylpropanesulfonic acid copolymer ("SIMULGEL EG" manufactured by SEPIC Co., Ltd.) | 0.5 |

<Preparation>

Components (1) to (8) were mixed and uniformly dissolved at 70° C. (oil phase). On the other hand, components (9) to (16) were mixed and uniformly dissolved at 70° C. (water phase). The emulsification was carried out with a homomixer while gradually adding the oil phase to the water phase maintained at 70° C. The emulsion particle size was 5 μm. After the completion of emulsification, the desired hair styling cream was obtained by rapidly cooling to 40° C. or lower.

<Product Properties>

For the obtained hair styling cream, similar evaluations to Test Examples 3 and 4 were conducted. As a result, it was found that the vitamin E derivative of Production Example 11 had an excellent emulsifying ability and the feeling in use was excellent (evaluation of feeling in use: the affinity for the skin, sticky feeling, light fresh feeling, and permeation feeling were all ⊚).

Example 9

O/W Emulsion Foundation

| (Component) | (Mass %) |
|---|---|
| (1) Liquid lanolin | 2.0 |
| (2) Liquid paraffin | 4.0 |
| (3) 2-ethylhexyl 2-ethylhexanoate | 5.0 |
| (4) Glyceryl monostearate | 0.1 |
| (5) Ethylene glycol dioleate/polyethylene glycol ("EMALEX 600 dio" manufactured by Nihon-Emulsion Co., Ltd.) | 0.5 |
| (6) Vitamin E derivative of Production Example 12 | 2.5 |
| (7) Perfume | 0.1 |
| (8) Ion-exchanged water | Balance |
| (9) Dipropylene glycol | 2.5 |
| (10) Ethanol | 1.0 |
| (11) Paraben | 0.1 |
| (12) Talc | 3.0 |
| (13) Titanium dioxide | 5.0 |
| (14) Red iron oxide (Colcothar) | 0.5 |
| (15) Yellow iron oxide | 1.4 |
| (16) Black iron oxide | 0.1 |

<Preparation>

Components (1) to (7) were mixed and uniformly dissolved at 70° C. (oil phase). On the other hand, components (8) to (16) were mixed and uniformly dissolved at 70° C. (water phase). The emulsification was carried out with a homomixer while gradually adding the oil phase to the water phase maintained at 70° C. The emulsion particle size was 10 to 20 μm. After the completion of emulsification, the desired O/W emulsion foundation was obtained by rapidly cooling to 40° C. or lower.

<Product Properties>

For the obtained O/W emulsion foundation, a similar evaluation to Test Example 2 was conducted. As a result, it was found that the vitamin E derivative of Production Example 12 had an excellent emulsifying ability and the feeling in use was excellent.

Example 10

O/W Emulsion Sunscreen

| (Component) | (Mass %) |
|---|---|
| (1) Octyl paramethoxycinnamate | 6.0 |
| (2) Glyceryl octyl diparamethoxycinnamate | 2.0 |
| (3) 4-tert-butyl-4'-methoxybenzoylmethane | 2.0 |
| (4) Pentaerythritol tetra(octanoate/paramethoxycinnamate) | 1.0 |
| (5) Isononyl isononanoate | 2.5 |
| (6) Tripropylene glycol dineopentanoate | 2.5 |
| (7) Decamethylcyclopentasiloxane | 2.0 |
| (8) Dimethylpolysiloxane (6 mPa·s) | 1.0 |
| (9) Vitamin E derivative of Production Example 13 | 5.0 |
| (10) Polyether-modified silicone (HLB 10) | 1.0 |
| (11) Ion-exchanged water | Balance |
| (12) Ethanol | 3.0 |
| (13) Ammonium polyacrylate ("SIMULGEL A" manufactured by SEPIC Co., Ltd.) | 0.5 |
| (14) Perfume | 0.1 |
| (15) Hydrophilic fine titanium oxide ("Titanium oxide MT 062" manufactured by Tayca corporation) | 1.0 |

<Preparation>

Components (1) to (7) were mixed and uniformly dissolved at 70° C. (oil phase). On the other hand, components (8) to (16) were mixed and uniformly dissolved at 70° C. (water phase). The emulsification was carried out with a homomixer while gradually adding the oil phase to the water phase maintained at 70° C. The emulsion particle size was 10 to 15 μm. After the completion of emulsification, the desired O/W emulsion sunscreen was obtained by rapidly cooling to 40° C. or lower.

<Product Properties>

For the obtained O/W emulsion sunscreen, a similar evaluation to Test Example 3 was conducted. As a result, it was found that the vitamin E derivative of Production Example 13 had an excellent emulsifying ability and the feeling in use was excellent.

Example 11

Whitening Skin Cream

| (Component) | (Mass %) |
|---|---|
| (1) Hydrogenated polyisobutene | 2.0 |
| (2) Decamethylcyclopentasiloxane | 6.0 |
| (3) 2-ethylhexyl 2-ethylhexanoate | 3.0 |
| (4) Vitamin E derivative of Production Example 14 | 3.0 |
| (5) Cetyl alcohol | 2.5 |
| (6) Batyl alcohol | 2.5 |
| (7) Perfume | 0.1 |
| (8) Ion-exchanged water | Balance |
| (9) 1,3-butylene glycol | 3.0 |
| (10) Tranexamic acid | 2.0 |
| (11) Ascorbic acid phosphate magnesium ester | 1.0 |
| (12) Paraben | 0.15 |
| (13) Ethanol | 3.0 |
| (14) Sodium hydroxide | 0.4 |
| (15) Alkyl-modified carboxyvinyl polymer | 0.5 |
| (16) Citric acid | 0.09 |
| (17) Sodium citrate | 0.01 |

<Preparation>

Components (1) to (7) were mixed and uniformly dissolved at 70° C. (oil phase). On the other hand, components (8) to (17) were mixed and uniformly dissolved at 70° C. (water phase). The emulsification was carried out with a homomixer while gradually adding the oil phase to the water phase maintained at 70° C. The emulsion particle size was 10 to 15 μm. After the completion of emulsification, the desired whitening skin cream was obtained by rapidly cooling to 40° C. or lower.

<Product Properties>

For the obtained whitening skin cream, similar evaluations to Test Examples 3 and 4 were conducted. As a result, it was found that the vitamin E derivative Production Example 14 had an excellent emulsifying ability and the feeling in use was excellent (evaluation of feeling in use: the affinity for the skin, sticky feeling, light fresh feeling, and permeation feeling were all ⊚).

Example 12

Whitening Skin Cream

| (Component) | (Mass %) |
|---|---|
| (1) α-olefin oligomer | 3.0 |
| (2) Dimethylpolysiloxane (6 mPa·s) | 5.0 |
| (3) Di-2-ethylhexyl succinate | 2.0 |
| (4) Vitamin B derivative of Production Example 15 | 3.0 |
| (5) Cetyl alcohol | 2.5 |
| (6) Batyl alcohol | 2.5 |
| (7) Perfume | 0.1 |
| (8) Ion-exchanged water | Balance |
| (9) 1,3-butylene glycol | 3.0 |
| (10) Trimethylglycine | 1.0 |
| (11) Potassium 4-methoxysalicylate | 2.0 |
| (12) Phenoxyethanol | 0.15 |
| (13) Ethanol | 3.0 |
| (14) Sodium hydroxide | 0.4 |
| (15) Dimethylacrylamide/2-acrylamide-2-methylpropanesulfonic acid copolymer ("SUpolymer G-1" manufactured by Toho Chemical Industry Co., Ltd.) | 0.5 |
| (16) Citric acid | 0.09 |
| (17) Sodium citrate | 0.01 |

<Preparation>

Components (1) to (7) were mixed and uniformly dissolved at 70° C. (oil phase). On the other hand, components (8) to (17) were mixed and uniformly dissolved at 70° C. (water phase). The emulsification was carried out with a homomixer while gradually adding the oil phase to the water phase maintained at 70° C. The emulsion particle size was 10 to 15 μm. After the completion of emulsification, the desired whitening skin cream was obtained by rapidly cooling to 40° C. or lower.

<Product Properties>

For the obtained whitening skin cream, similar evaluations to Test Examples 3 and 4 were conducted. As a result, it was found that the vitamin E derivative of Production Example 15 had an excellent emulsifying ability and the feeling in use was excellent (evaluation of feeling in use: the affinity for the skin, sticky feeling, light fresh feeling, and permeation feeling were all ⊚).

Example 13

Whitening Skin Cream

| (Component) | (Mass %) |
|---|---|
| (1) Hydrogenated polyisobutene | 3.0 |
| (2) Dimethylpolysiloxane (6 mPa · s) | 5.0 |
| (3) Cetyl ethylhexanoate | 2.0 |
| (4) Vitamin E derivative of Production Example 16 | 4.0 |
| (5) Stearyl alcohol | 1.0 |
| (6) Behenyl alcohol | 1.5 |
| (7) Perfume | 0.1 |
| (8) Ion-exchanged water | Balance |
| (9) 1,3-butylene glycol | 3.0 |
| (10) Trimethylglycine | 1.0 |
| (11) Potassium 4-methoxysalicylate | 1.0 |
| (12) Ascorbic acid glucoside | 1.0 |
| (13) Phenoxyethanol | 0.15 |
| (14) Ethanol | 3.0 |
| (15) Sodium hydroxide | 0.4 |
| (16) Agar | 0.2 |
| (17) Citric acid | 0.09 |
| (18) Sodium citrate | 0.01 |

<Preparation>

Components (1) to (7) were mixed and uniformly dissolved at 70° C. (oil phase). On the other hand, components (8) to (17) were mixed and uniformly dissolved at 70° C. (water phase). The emulsification was carried out with a homomixer while gradually adding the oil phase to the water phase maintained at 70° C. The emulsion particle size was 10 to 15 μm. After the completion of emulsification, the desired whitening skin cream was obtained by rapidly cooling to 40° C. or lower.

<Product Properties>

For the obtained whitening skin cream, similar evaluations to Test Examples 3 and 4 were conducted. As a result, it was found that the vitamin E derivative of Production Example 16 had an excellent emulsifying ability and the feeling in use was excellent (evaluation of feeling in use: the affinity for the skin, sticky feeling, light fresh feeling, and permeation feeling were all ⊚).

What is claimed is:

1. A cosmetic containing a vitamin E derivative represented by the following formula (I) or a salt thereof:

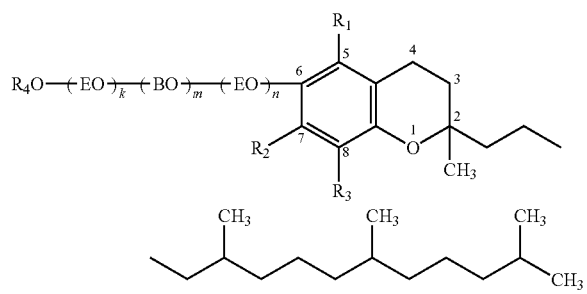

(I)

wherein
(a) $R_1$, $R_2$, and $R_3$ independently represent a hydrogen atom or a methyl group;
(b) $R_4$ represents a hydrogen atom, an alkanoyl group having carbon atoms 1 to 6, an alkyl group having 1 to 6 carbon atoms, an $SO_3H$ group, a $P(O)(OH)_2$ group, a $CH_2COOH$ group, or a $COCH_2CH(SO_3H)COOH$ group;
(c) EO represents an ethylene oxide group;
(d) BO represents a butylene oxide group; k and n are independently chosen from 0 to 30, with the proviso that k and n are not both simultaneously zero; and
(e) m is from 1 to 30.

2. The cosmetic of claim 1 in which $R_1$, $R_2$ and $R_3$ in formula (I) are methyl groups.

3. The cosmetic of claim 1, wherein $R_1$ and $R_3$ in formula (I) are methyl groups and $R_2$ is a hydrogen atom.

4. The cosmetic of claim 1, wherein $R_1$ in formula (I) is a hydrogen atom and $R_2$ and $R_3$ are methyl groups.

5. The cosmetic of claim 1, wherein $R_1$ and $R_2$ in formula (I) are hydrogen atoms and $R_3$ is a methyl group.

6. The cosmetic of claim 1, wherein $R_4$ in formula (I) is a hydrogen atom.

7. The cosmetic of claim 1, wherein $R_4$ in formula (I) represents any one of an alkanoyl group having 1 to 6 carbon atoms, an alkyl group having 1 to 6 carbon atoms, an $SO_3H$ group, a $P(O)(OH)_2$ group, a $CH_2COOH$ group, or a $COCH_2CH(SO_3H)COOH$ group.

8. A solubilizing agent comprising a vitamin E derivative represented by the following formula (I) or a salt thereof:

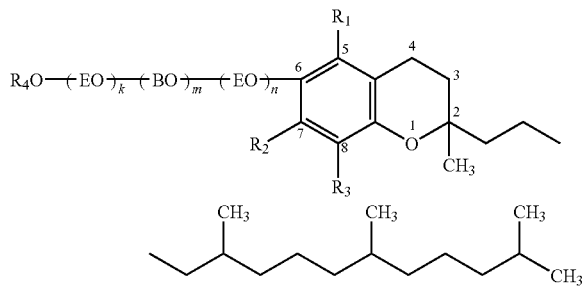

(I)

wherein
(a) $R_1$, $R_2$, and $R_3$ independently represent a hydrogen atom or a methyl group;
(b) $R_4$ represents a hydrogen atom, an alkanoyl group having carbon atoms 1 to 6, an alkyl group having 1 to 6 carbon atoms, an $SO_3H$ group, a $P(O)(OH)_2$ group, a $CH_2COOH$ group, or a $COCH_2CH(SO_3H)COOH$ group;
(c) EO represents an ethylene oxide group;
(d) BO represents a butylene oxide group; k and n are independently chosen from 0 to 30, with the proviso that k and n are not both simultaneously zero; and
(e) m is from 1 to 30.

9. The cosmetic of claim 2, wherein $R_4$ in formula (I) is a hydrogen atom.

10. The cosmetic of claim 3, wherein $R_4$ in formula (I) is a hydrogen atom.

11. The cosmetic of claim 4, wherein $R_4$ in formula (I) is a hydrogen atom.

12. The cosmetic of claim 5, wherein $R_4$ in formula (I) is a hydrogen atom.

13. The cosmetic of claim 2, wherein $R_4$ in formula (I) represents any one of an alkanoyl group having 1 to 6 carbon atoms, an alkyl group having 1 to 6 carbon atoms, an $SO_3H$ group, a $P(O)(OH)_2$ group, a $CH_2COOH$ group, or a $COCH_2CH(SO_3H)COOH$ group.

14. The cosmetic of claim 3, wherein $R_4$ in formula (I) represents any one of an alkanoyl group having 1 to 6 carbon atoms, an alkyl group having 1 to 6 carbon atoms, an $SO_3H$ group, a $P(O)(OH)_2$ group, a $CH_2COOH$ group, or a $COCH_2CH(SO_3H)COOH$ group.

15. The cosmetic of claim 4, wherein $R_4$ in formula (I) represents any one of an alkanoyl group having 1 to 6 carbon atoms, an alkyl group having 1 to 6 carbon atoms, an $SO_3H$ group, a $P(O)(OH)_2$ group, a $CH_2COOH$ group, or a $COCH_2CH(SO_3H)COOH$ group.

16. The cosmetic of claim 5, wherein $R_4$ in formula (I) represents any one of an alkanoyl group having 1 to 6 carbon atoms, an alkyl group having 1 to 6 carbon atoms, an $SO_3H$ group, a $P(O)(OH)_2$ group, a $CH_2COOH$ group, or a $COCH_2CH(SO_3H)COOH$ group.

\* \* \* \* \*